United States Patent [19]
Siemers et al.

[11] Patent Number: 6,132,722
[45] Date of Patent: Oct. 17, 2000

[54] RECOMBINANT ANTIBODY-ENZYME FUSION PROTEINS

[75] Inventors: Nathan O. Siemers, Hamilton Township, N.J.; Susan Yarnold; Peter D. Senter, both of Seattle, Wash.

[73] Assignee: Bristol-Myers Squibb Company, New York, N.Y.

[21] Appl. No.: 09/070,637

[22] Filed: Apr. 30, 1998

Related U.S. Application Data

[60] Provisional application No. 60/045,888, May 7, 1997.

[51] Int. Cl.$^7$ .................. A61K 39/395; A61K 47/16; C12N 9/96
[52] U.S. Cl. .................. 424/192.1; 424/94.3; 514/12; 435/188; 530/388.1; 530/388.2; 530/338.8; 530/388.85; 530/866; 530/867; 530/324
[58] Field of Search .................. 435/188, 188.5, 435/191, 228, 231, 230; 429/192.1, 94.3; 514/12; 530/388.1, 388.2, 388.8, 388.85, 866, 867, 329

[56] References Cited

U.S. PATENT DOCUMENTS 4,975,278  12/1990  Senter et al. .

FOREIGN PATENT DOCUMENTS

WO94/12520  6/1994  WIPO .

OTHER PUBLICATIONS

Yeh et al., "Cell Surface Antigens of Human Melanoma identified by Monoclonal Antibody," *Proc. Natl. Acad. Sci. USA* 76:2927–2931 (Jun., 1979).

Woodbury et al., "Identification of a Cell Surface Protein, p97, in Human Melanomas and Certain Other Neoplasms," *Proc. Natl. Acad. Sci. USA* 77:2183–2187 (Apr., 1980).

Brown et al., "Quantitative Analysis of Melanoma–Associated Antigen p97 in Normal and neoplastic Tissues," *Proc. Natl. Acad. Sci. USA* 78:539–543 (Jan., 1981).

Brown et al., "Structural characterization of Human Melanoma–Associated Antigen p97 with Monoclonal Antibodies," *J. Immunol.* 127:539–546 (Aug., 1981).

Bosslet et al., "Molecular and Functional Characterisation of a Fusion Protein Suited for Tumour Specific Prodrug Activation," *Br. J. Cancer* 65:234–238 (1992).

Goshorn et al., "Genetic Construction, Expression, and Characterization of a Single Chain Anti–Carcinoma Antibody Fused to β–Lactamase," *Cancer Res.* 53:2123–2127 (May 1, 1993).

Senter et al., "Generation of Cytotoxic Agents by Targeted Enzymes," *Bioconjugate Chem.* 4:3–9 (1993).

DeSutter et al., "A bifunctional Murine::Human Chimeric Antibody with One Antigen–Binding Arm Replaced by Bacterial β–Lactamase," *Mol. Immunol.* 31:261–267 (1994).

Bosslet et al., "Tumor–Selective Prodrug Activation by Fusion Protein–Mediated Catalysis," *Cancer Res.* 54:2151–2159 (Apr. 15, 1994).

Wallace et al., "Intratumoral Generation of 5–Fluorouracil Mediated by an Antibody–Cytosine Deaminase Conjugate in Combination with 5–Fluorocytosine," *Cancer Res.* 54:2719–2723 (May 15, 1994).

Jungheim and Shepherd, "Design of Antitumor Prodrugs: Substrates for Antibody Targeted Enzymes," *Chem. Rev.* 94:1553–1566 (1994).

Bagshawe et al., "Antibody Directed Enzyme Prodrug Therapy (ADEPT)," *Ann. Oncol.* 5:897–891 (1994).

Rodrigues et al., "Development of a Humanized Disulfide–Stabilized Anti–p185$^{HER2}$ Fv–β–Lactamase Fusion Protein for Activation of a Cephalosporin Doxorubicin Prodrug," *Cancer Res.* 55:63–70 (Jan. 1, 1995).

Svensson et al., "In Vitro and In Vivo Activities of a Doxorubicin Prodrug in Combination with Monoclonal Antibody β–Lactamase Conjugates," *Cancer Res.* 55:2357–2365 (Jun. 1, 1995).

Kerr et al., "Regressions and Cures of Melanoma Xenografts Following Treatment with Monoclonal Antibody β–Lactamase Conjugates in Combination with Anticancer Prodrugs," *Cancer Res.* 55:3558–3563 (Aug. 15, 1995).

Siemers et al., "Modifying the Specificity and Activity of the *Enterobacter cloacae* P99 β–Lactamase by Mutagenesis within an M13 Phage Vector," *Biochem.* 35:2104–2111 (1996).

Siemers et al., "Construction, Expression, and Activities of L49–sFv–β–Lactamase, a Single–Chain Antibody Fusion Protein for Anticancer Prodrug Activation," *Bioconjugate Chem.* 8:510–519 (1997).

*Primary Examiner*—Yvonne Eyler
*Assistant Examiner*—Anne L. Holleran
*Attorney, Agent, or Firm*—Townsend and Townsend and Crew LLP

[57] ABSTRACT

The invention is related to recombinantly produced fusion polypeptides comprising antibody $V_H$ and $V_L$ sequences operatively linked to a β-lactamase for use in the delivery of cytotoxic drugs to tumor cells.

8 Claims, 11 Drawing Sheets

FIG. 4A

AATTAATACGACTCACTATAGGGGAATTGTGAGCGGATAACAATTCCCCTCTAGAAATAATTTTGTTTAACTTTAAGAAGGAGATATACA
                                                                                L49 HEAVY CHAIN V
TATGAAATACCTGCTGCCGACCGCTGCTGCTGGTCTGCTGCTCCTCGCTGCCCAGCCGGCCATGGCC GAGGTGCAGCTTCAGGAGTCAGG
  1 M  K  Y  L  L  P  T  A  A  A  G  L  L  L  L  A  A  Q  P  A  M  A   E  V  Q  L  Q  E  S  G

ACCTAGCCTCGTGAAACCTTCTCAGATCTGTGTCCCTCACCTGTTCTGTGTTACTGGCGACTCCATCACCAGTGGTTACTGGAACTGGATCCG
 9 P  S  L  V  K  P  S  Q  T  L  S  L  T  C  S  V  T  G  D  S  I  T  S  G  Y  W  N  W  I  R

GAAGTTCCCAGGGAATAAACTTGAATATATGGGTTACATAAGCGACAGTGGTATCCATCTACAATCCATCTCAAAAGTCGCATTTC
39 K  F  P  G  N  K  L  E  Y  M  G  Y  I  S  D  S  G  I  T  Y  Y  N  P  S  L  K  S  R  I  S

CATCACTCGAGACACATCCAAGAACCATACTACCTCCAGTTGAATTTTGTGACTGCTGAGGACACAGCCACATATAACTGTGCAAGAAG
69 I  T  R  D  T  S  K  N  Q  Y  Y  L  Q  L  N  F  V  T  A  E  D  T  A  T  Y  N  C  A  R  R
                                                                                        218 LINKER
GACTCTGGCTACTACTATGCTATGGACTACTGGGGTCAAGGAACCTCTGTCACCGTCTCCTCA ggtcgacgtcggctctggcaaacc
99 T  L  A  T  T  Y  Y  A  M  D  Y  W  G  Q  G  T  S  V  T  V  S  S  G  S  T  S  G  K  P
                                  L49 LIGHT CHAIN V
gggctctggcgaaggctctaccagaggc GATTTTGTGATGACCCAAACTCCACTCTCCCTGCCTGTCAGTCTTGGAGATCAAGCCTCCAT
129 G  S  G  E  G  S  T  K  G   D  F  V  M  T  Q  T  P  L  S  L  P  V  S  L  G  D  Q  A  S  I CTCTTGCAGGGTGCTAGTCAGTCAGAGAGTTGTACACAGTAATGGAAACACCTATTGGTACCTGCAGAAGCCAGGCCAGTCTCCAAAGCT
159 S  C  R  A  S  Q  S  L  V  H  S  N  G  N  T  Y  L  H  W  Y  L  Q  K  P  G  Q  S  P  K  L CCTGATCTACAAAGTTTCCAACCGATTTTCTGGGGTCCCAGACAGGTTCAGTGGCAGTGGATCAGGGACAGATTTCACACTCAAGATCAG
189 L  I  Y  R  V  S  N  R  F  S  G  V  P  D  R  F  S  G  S  G  S  G  T  D  F  T  L  K  I  S CAGAGTGGAGGCTGAGGATCTGGGAGTTTATTTCTGCTCTCAAAGTACACATGTTCCTCCGACGTTCGGTGGAGGCACCAAGCTGGAAAT
219 R  V  E  A  E  D  L  G  V  Y  F  C  S  Q  S  T  H  V  P  P  T  F  G  G  G  T  K  L  E  I
          BETA-LACTAMASE
CAAACGG ACGCCCAGTGTCAGAAAAACAGCTGGCGGAGGTGGTCGCGAATACGATTACCCCGCTGATGAAGGCCCAATCTGTTCCAGGCAT
249 K  R   T  P  V  S  E  K  Q  L  A  E  V  V  A  N  T  I  T  P  L  M  K  A  Q  S  V  P  G  M GCGGGTGCCGTTATTTATCAGGGAAAACCGCACTATTACACATTTGGCAAGGCCGATATCGCGGCGAATAAACCCGTTACGCCTCAGAC
279 A  V  A  V  I  Y  Q  G  K  P  H  Y  Y  T  F  G  K  A  D  I  A  A  N  K  P  V  T  P  Q  T

FIG. 4B

```
    CCTGTTCGAGCTGGGGTTCTATAAGTAAAACCTTCACCGGGCGTTTAGGTGGGGATGCCATTGCTCGCGGTGAAATTTCGCTGGACGATGC
309 L  F  E  L  G  S  I  S  K  T  F  T  G  V  L  G  G  D  A  I  A  R  G  E  I  S  L  D  D  A

GGTGACCAGATACTGGCCACACAGCTGACGGGCAAGCAGTGGCAGGGTATTCGTATGCTGGATCTCGCCACCTACACCGCTGGCGGCCTGCC
339 V  T  R  Y  W  P  Q  L  T  G  K  Q  W  Q  G  I  R  M  L  D  L  A  T  Y  T  A  G  G  L  P

GCTACAGGTACCGGATGAGGTCACGGATAACGCCTCCCTGCTGCGCTTTTATCAAAACTGGTAGCCGCAGTGGAAGCCTGGCACAACGCG
369 L  Q  V  P  D  E  V  T  D  N  A  S  L  L  R  F  Y  Q  N  W  Q  P  Q  W  K  P  G  T  T  R

TCTTTACGGCCAACGCCTCAAGCTGGACCATCGGACCATCGACCATCCGGACCATTACGCCTCAAACCTTCTGGCATGCCCATATCGTCGACGGTAAAGC
399 L  Y  A  N  A  S  I  G  L  F  G  A  L  A  V  K  P  S  G  M  P  Y  E  Q  A  M  T  T  R  V

CCTTAAGCCGCTCAAGCTGGACCATACCTGGATTAACGTGCCGAAAGCTGCCGAAGCCTATGGCGGCAAAGCCATTACGCCGCTATCGTCGACGGTAAAGC
429 L  K  P  L  K  L  D  H  T  W  I  N  V  P  K  A  E  E  A  H  Y  A  W  G  Y  R  D  G  K  A

GGTGCGCGTTTCGCCGGGTATGCTGGATGCACAAGCCTCACTTAAGCCTGAAACTGCAGGGCATCGCGCTGGCAGTCGCGCTACTGGCGTCATGGTATCAGGG
459 V  R  V  S  P  G  M  L  D  A  Q  A  Y  G  I  A  L  Q  K  G  I  A  L  Q  S  R  Y  W  R  I  G  S  M  Y  Q  G

GGGCCCCGAGAACGTTGCTGATGCCTCACTTAAGCCTGAAACTGCAGGGCCAACACGGTTGGTCCAACCGTGGTTGTTGAGCTGGCCGTTGCCGT
489 A  P  E  N  V  A  D  A  S  L  K  Q  G  I  A  L  Q  N  T  V  V  E  N  V  A  L  A  P  L  P  V

TCTGGGGCTGGGAGATGCTCAACTGGCCGGTCGAGGCCCCCGGTCAAAGCGTCCTGGGTCCATAAAACGGGCTCTACTGGGCTTTGGCAGCTACGTGGCCTT
519 L  G  W  E  M  L  N  W  P  V  E  A  N  T  V  V  H  K  T  G  S  T  G  G  F  G  S  Y  V  A  F

GGCAGAAGTGAATCCACCGGCTCCCCCGGTTGTCAAAGCGTCCTGGGTCCATAAAACGGGCTCTACTGGGCTTTGGCAGCTACGTGGCCTT
549 A  E  V  N  P  P  A  P  P  V  K  A  S  W  V  H  K  T  G  S  T  G  G  F  G  S  Y  V  A  F

TATTCCTGAAAAGCAGATCGGTATTGTGATGCTCGGAATACAAGCTATCCGAACCGGACACCGTTGAGCGACATACCATATCctgaGAATTCGAGCT
579 I  P  E  K  Q  I  G  I  V  M  L  A  N  T  S  Y  P  N  P  A  R  V  E  A  A  Y  H  I  L  E ggcgctacagtagactagtGAATTCGAGCT
609 A  L  Q  *
```

NON-REDUCING    REDUCING

IPTG CONCENTRATION (μM)

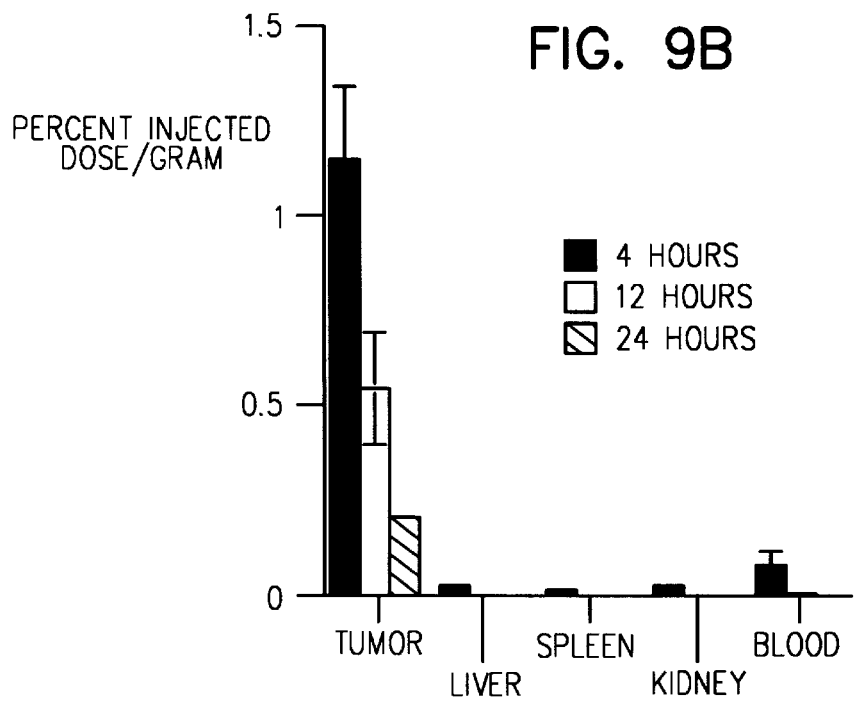
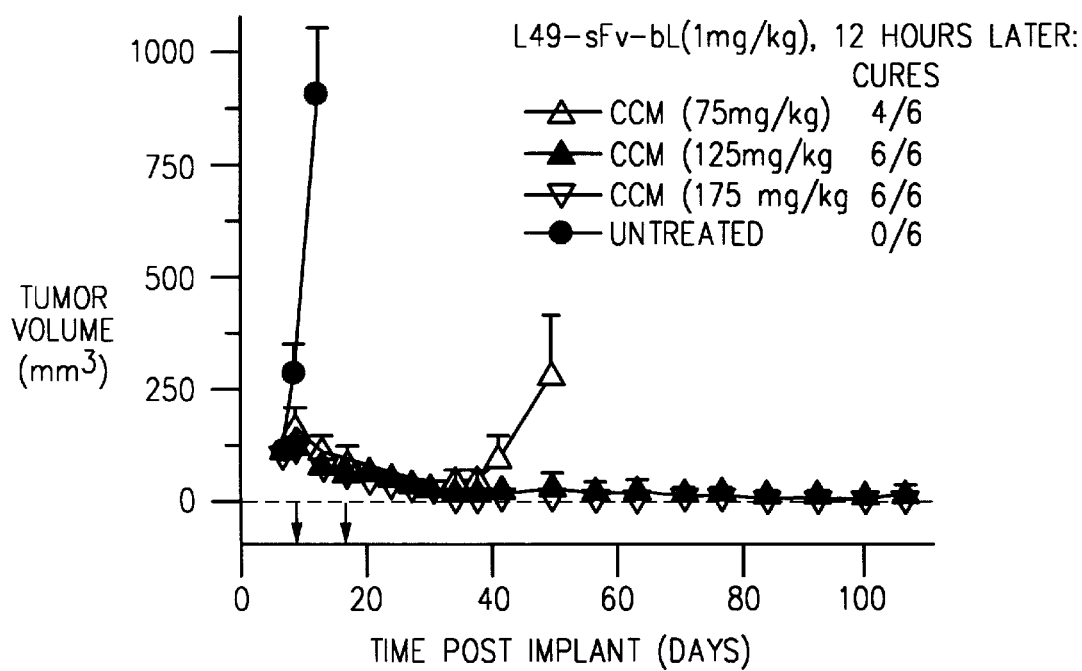

RECOMBINANT ANTIBODY-ENZYME FUSION PROTEINS

This application claims the benefit of U.S. Provisional Application Ser. No. 60/045,888, filed May 7, 1997.

BACKGROUND OF THE INVENTION

A considerable amount of attention has been directed towards the use of monoclonal antibody-enzyme conjugates in combination with suitable prodrugs for the selective delivery of chemotherapeutic agents to tumors (reviewed in Senter et al., *Bioconiugate Chem.*, 4:3–9 (1993); Jungheim et al., *Chem Rev.*, 94:1553–1566 (1994); Bagshawe et al., *Ann. Oncol.*, 5:879–891 (1994)). The monoclonal antibody (mAb) portions of these immunoconjugates recognize tumor-selective antigens and are capable of delivering the enzymes to tumor masses. Once tumor localization and systemic conjugate clearance has taken place, a non-cytotoxic prodrug form of a chemotherapeutic drug is administered which is converted into an active drug by the targeted enzyme. This leads to the selective delivery of anticancer drugs to sites of neoplasia. Pharmacokinetic studies have shown that the intratumoral drug concentrations resulting from mAb-enzyme/prodrug combinations can be significantly greater than that achieved by systemic drug administration (Bosslet et al., *Cancer Res.*, 54:2151–2159 (1994); Svensson et al., *Cancer Res.*, 55:2357–2365 (1995); Wallace et al., *Cancer Res.*, 54:2719–2327 (1994)). This probably accounts for the observed antitumor activities, which include complete tumor regressions and cures in a number of different models for human cancer (Springer et al., *Eur. J. Cancer*, 27:1361–1366 (1991); Meyer et al., *Cancer Res.*, 53:3956–3963 (1993); Eccles et al., *Cancer Res.*, 54:5171–5177 (1994); Kerr et al., *Cancer Res.*, 55:3558–3563 (1995)).

Kerr et al. disclosed the use of antibodies against the human p97 (melanotransferrin) tumor antigen for the delivery of β-lactamase (bL) to tumor cells (Kerr et al., *Cancer Res.*, 55:3558–3563 (1995)). This antigen has been found to be overexpressed on a majority of clinical melanoma isolates and is also observed on many human carcinomas (Woodbury et al., *Proc. Natl. Acad. Sci. (USA)*, 77:2183–2187 (1980); Brown et al., *J. Immun.*, 127:539–545 (1981), Brown et al., *Proc. Natl. Acad. Sci. (USA)*, 78:539–543 (1981); Rose et al., *Proc. Natl. Acad. Sci. (USA)* (1986)). Significant antitumor activities have been obtained using the combination of a chemically produced anti p97-Fab'-bL conjugate in combination with CCM (7-(4-carboxybutan-amido)cephalosporin mustard; Kerr et al., *Cancer Res.*, 55:3558–3563 (1995)), a cephalosporin containing prodrug of phenylenediamine mustard (PDM). These effects were observed in a melanoma tumor model that was resistant to the activities of PDM.

A major concern in the development of mAb-bL conjugates for clinical testing is conjugate uniformity. Typically, mAb-enzyme conjugates are prepared using bifunctional cross-linking reagents that react in a random fashion with exposed amino acid residues on the individual proteins. Immunoconjugates produced in this manner are microscopically heterogeneous due to the inherent lack of specificity of the cross-linking reagents. In addition, chemically prepared conjugates are typically isolated in low yields. Although recent reports describe alternative coupling chemistries that can afford higher yields of more homogeneous immunoconjugates (Mikolajczyk et al., *Bioconjugate Chem.*, 5:636–646 (1994); Werlen et al., *Bioconjugate Chem.*, 5:411–417 (1994); Werlen et al., *Tumor Targeting*, 1:251–258 (1995)), these methods still involve chemical modification steps that can contribute to product heterogeneity.

Genetically constructed fusion proteins offer an alternative method of producing homogeneous mAb-enzyme conjugates. There have now been reports describing the production, characterization, and activities of recombinant Fab, sFv, and disulfide stabilized Fv-enzyme fusion proteins (Bosslet et al., *Br. J. Cancer*, 65:234–238 (1992); Goshorn et al., *Cancer Res.*, 53:2123–2127 (1993); Rodrigues et al., *Cancer Res.*, 55:63–70 (1995)).

Thus, a need exists for homogeneous mAb-enzyme conjugates for use in combination with prodrugs. The instant invention addresses this need and more.

SUMMARY OF THE INVENTION

One aspect of the invention is a fusion polypeptide comprising antibody variable light and heavy region amino acid sequences specific for a melanoma associated antigen operatively linked to a β-lactamase.

A further aspect of the invention is a method for the delivery of a cytotoxic agent to a tumor cell comprising the administration of a fusion polypeptide comprising antibody variable light and heavy region sequences operatively linked to a β-lactamase, wherein the fusion polypeptide is reactive with a tumor cell antigen and the fusion polypeptide converts a prodrug to a cytotoxic drug, and the administration of an effective amount of the prodrug.

BRIEF DESCRIPTION OF THE DRAWINGS

FIGS. 4A and 4B depicts the nucleotide (SEQ ID. NO: 19) and amino acid (SEQ ID. NO: 20) sequence for L49-sFv-bL including the PelB leader sequence.

FIG. 5A depicts non-reducing and reducing SDS-PAGE analysis of recombinant sp97 and p97 antigen.

FIG. 6A depicts the induction of L49-sFv-bL at varying IPTG concentrations (30° C., total cellular protein, 12% tris-glycine SDS-PAGE, Commassie staining, non-reducing conditions). The band corresponding to L49-sFv-bL is indicated with arrows. FIG. 6B depicts a Western analysis with rabbit polyclonal anti-bL. Lane 1: periplasm; Lane 2: L49-sFv-bL standard (12% tris-glycine SDS-PAGE, non-reducing conditions). FIG. 6C depicts the purification of L49-sFv-bL. Lane 1, periplasm; Lane 2, flow through from the sp97 affinity column; Lane 3, material that eluted from the sp97 column at pH 11; Lane 4, material that bound and eluted off the phenylboronic acid column (12i tris-glycine SDS-PAGE, Commassie staining, non-reducing conditions). FIG. 6D is a representative comparison of L49-sFv-bL to chemically prepared L49-Fab'-bL. Lane 1, L49-Fab'-bL; Lane 2, L49-sFv-bL (10% tris-glycine SDS-PAGE, Commassie staining, non-reducing conditions).

FIGS. 9A and 9B depict pharmacokinetics of L49-sFv-bL in nude mice (3 animals/group). L49-sFv-bL was injected intravenously, tissues were removed and extracted at the indicated times, and the β-lactamase activity was determined using nitrocefin as a substrate. FIG. 9A depicts clearance of L49-sFv-bL from the blood. Injected dose was 4 mg/kg. FIG. 9B depicts L49-sFv-bL levels in subcutaneous 3677 melanoma tumors and in normal tissues. Injected dose was 1 mg/kg.

FIGS. 10A–10D. Therapeutic effects of L49-sFv-bL/CCM combinations in nude mice (six mice/group) with subcutaneous 3677 melanoma xenografts. Conjugates were injected, followed at various times by CCM (arrows on the X-axis). The average tumor volumes were reported until most or all of the animals were cured (tumors that became non-palpable for ≧10 tumor volume doubling times), or until an animal was removed from the experiment due to tumor outgrowth. FIG. 10A. L49-sFv-bL (1 mg/kg/injection) 12 h before CCM. FIG. 10B. L49-sFv-bL (1 mg/kg/injection) 24 h before CCM. FIG. 10C. L49-sFv-bL (4 mg/kg/injection) 24 h before CCM. FIG. 10D. L49-sFv-bL (4 mg/kg/injection) 48 h before CCM.

DETAILED DESCRIPTION OF THE INVENTION

Figure 1:
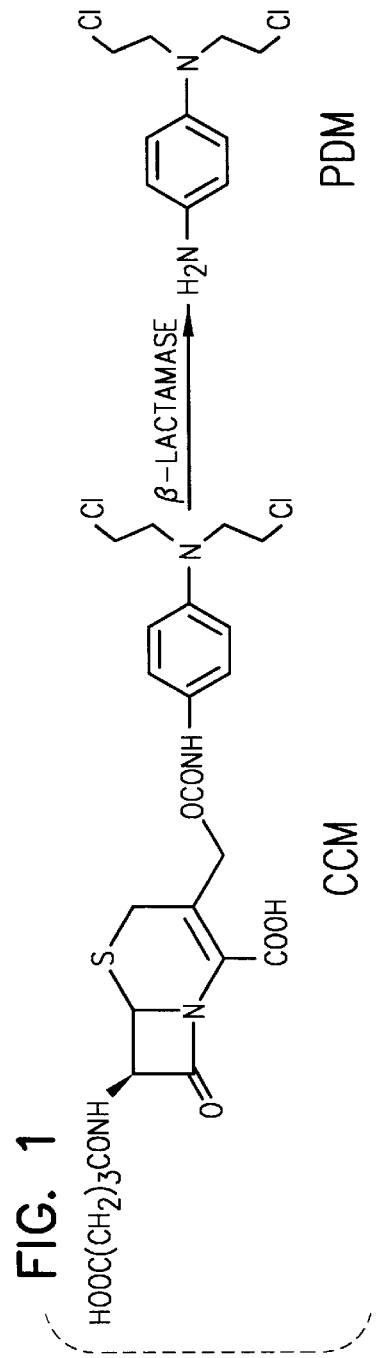
FIG. 1 depicts the structures of the cephalosporin mustard prodrug CCM and the parent drug phenylenediamine mustard PDM.

The present invention encompasses pharmaceutical compositions, combinations and methods for treating cancers and other tumors. More particularly, the invention includes combinations comprising the antibody-enzyme fusion polypeptides of the invention and a corresponding prodrug or prodrugs for use in a method for treating tumors wherein a mammalian host is treated in a pharmaceutically acceptable manner with a pharmaceutically effective amount of an antibody-enzyme fusion polypeptide and a pharmaceutically effective amount of a prodrug or prodrugs. The combination and methods of this invention are useful in treating any mammal, including humans, dogs, cats, and horses.

In some embodiments the enzyme component of the antibody-enzyme fusion is β-lactamase. The β-lactamase (bL) can be a class A, B, C, or D enzyme (Ledent et al., Biochem. J., 292:555–562 (1993); Felici et al., Biochem. J., 291:151–155 (1993)). Preferably, the bL is a class C enzyme. More preferably, the bL is an Enterobacter cloacae enzyme (Dubus et al., Biochem. J., 301:485–494 (1994)). The enzyme can be wild-type or mutant. For example, the E. cloacae P99 bL fusion protein can be substituted at amino acid residues 537–541 (Gly Ser Asp Ser Lys (SEQ ID. NO: 1)). Possible substitutions at this region include Thr Ser Phe Gly Asn (SEQ ID. NO: 2), Ala Ser Ala Arg Arg (SEQ ID. NO: 3), Asn Asn Ala Gly Tyr (SEQ ID. NO: 4), Glu Val Glu Ile Lys (SEQ ID. NO: 5), Leu Thr Ser Asn Arg (SEQ ID. NO: 6), Gly Ser Lyn Ser His (SEQ ID. NO: 7), Val Thy Arg Asn Gln (SEQ ID. NO: 8), Ile Val Asn Asn Lys (SEQ ID. NO: 9), Thr Ala Ile Pro Asp (SEQ ID. NO: 10) and Ile Thr Lys Pro Asp (SEQ ID. NO: 11) (Siemers et al., Biochemistry 35:2104–2111 (1996). A preferred mutant is Thr Ser Phe Gly Asn (SEQ ID. NO: 2).

The antibody component of the fusion can be obtained from any species. In an embodiment, the antibody is a murine monoclonal antibody directed against an antigen characteristic of a tumor cell to be targeted. Techniques for generating such monoclonal antibodies are well known in the art.

Antibodies can also be obtained from phage display and bacterial surface display libraries. This includes those produced from human tissue sources (to make human monoclonal antibodies) and combinatorial libraries of monoclonal antibodies produced by mutagenesis of CDR loops.

Typically, nucleic acid sequences encoding the variable regions of the light chains of the antibody are cloned by techniques well known in the art, such as by random hexamer primed reverse transcription reactions and PCR with signal sequence and constant region PCR primers (Jones et al., Biotechnology, 9:88–92 (1991)).

The corresponding DNA sequences are inserted into a vector of choice. Typically a secretory leader is operatively linked to the $V_H$ and $V_L$ region sequences. Any secretory leader can be used that will direct the secretion of the fusion protein into the periplasm of E. coli or other host, or into the medium. Exemplary secretory leaders include PelB, OmpA and StIII.

Typically the $V_H$ and $V_L$ region coding sequences are separated by a spacer that is generally greater than or equal to 15 amino acids. Examples include the sequence Gly Gly Gly Gly Ser Gly Gly Gly Gly Ser Gly Gly Gly Gly Ser (SEQ ID. NO: 12) and the sequence Gly Ser Thr Ser Gly Ser Gly Lys Pro Gly Ser Gly Glu Gly Ser Thr Lys Gly (SEQ ID. NO: 13) (218 linker). The $V_L$ region gene is linked in continuous reading frame with the enzyme.

The entire fusion construct can be replicated as part of a vector that can be propagated in a host of interest, including but not limited to bacterial, yeast, insect, and mammalian hosts.

The prodrugs are preferably cephalosporin derivatives of phenylenediamine mustard, doxorubicin, mitomycin C, paclitaxel, vinca alkaloids, and melphalan. Other anti-cancer agents with active amines, hydroxyl or thiol groups can be modified with cephalosporins to form drugs that are activated by β-lactamases.

According to a preferred embodiment, the antibody-enzyme fusion polypeptide is administered prior to the introduction of the prodrug into the host. Sufficient time should be allowed between administration of the conjugate and the prodrug to allow the antibody component of the conjugate to target and localize the enzyme to the tumor site. Such sufficient time may range from 4 hours to one week depending upon the conjugate used.

The conjugates and prodrugs of the invention can be administered using conventional modes of administration including, but not limited to, intravenous, intraperitoneal, oral, intralymphatic, or administration directly into the tumor. Intravenous administration is preferred.

The compositions of the invention-comprising the immunoconjugates or prodrugs-may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the antibody-enzyme conjugate may be disfavored because the conjugate proteins tend to be degraded in the stomach if taken orally, e.g., in tablet form.

The conjugate or prodrug compositions also preferably include conventional pharmaceutically acceptable carriers and adjuvants known in the art such as human serum albumin, ion exchangers, alumnia, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgement of the treating physician. Accordingly, the dosages of the immunoconjugates and prodrugs should be titrated to the individual patient.

Nevertheless, an effective dose of the antibody-enzyme conjugate of this invention may be in the range of from about 1.0 to about 100 mg/m$^2$. An effective dose of the prodrug of the invention will depend upon the particular prodrug used and the parent drug from which it is derived. Since the prodrug is less cytotoxic than the parent drug, dosages in excess of those recognized in the art for the parent drug may be used. For example, an effective dose of the cephalosporin mustard prodrugs may be in the range of about 500 mg/m$^2$.

In order that the invention described herein may be more fully understood, the following examples are set forth. It should be understood that these examples are for illustrative purposes only and are not to be construed as limiting the scope of this invention in any manner.

EXPERIMENTAL EXAMPLES

Materials. The *Enterobacter cloacae* P99 gene was obtained from the plasmid pNU363 (Galleni et al., *Biochem. J.*, 250:753–760 (1988)). The r2-1 bL was isolated from a library of *E. cloacae* enzymes in which the nucleotides corresponding to amino acids 286–290 were subjected to codon-based mutagenesis (Siemers et al., *Biochemistry*, 35:2104–2111 (1996)), and contains the residues Thr Ser Phe Gly Asn (SEQ ID. NO: 2) at these positions. L49-Fab'-bL was prepared as previously described by combining thiolcontaining Fab' fragments of the antibodies with maleimide-substituted bL, forming a thioether link between the two proteins (Svensson et al., *Bioconjugate Chem.*, 5:262–267 (1994)).

Isolation and Characterization of the L49 Antibody. The L49 producing hybridoma was developed using standard techniques as previously described for the isolation of other hybridomas (Yeh et al., *Proc. Natl. Acad. Sci. (USA)*, 76:2927–2931 (1979)). Balb/C mice were immunized repeatedly with the H2981 (lung carcinoma), CH3 (lung carcinoma), and W56 (melanoma) cell lines, all of which were derived from human tumors. Spleen cells from the immunized mice were hybridized with the neomycin gene transfected myeloma cell line P3X63-Ag8.563 (Yeh et al., *Proc. Natl. Acad. Sci. (USA)*, 76:2927–2931 (1979)). Standard selection and cloning yielded a hybridoma producing the L49 IgG1 antibody.

Scatchard analysis of L49 binding was performed by radiolabeling the mAb with [$^{125}$I]Iodogen to a specific activity of 0.3 mCi/mg protein. 3677 melanoma cells (Kerr et al., *Cancer Res.*, 55:3558–3563 (1995)) in 96-well plates (13,000 cells/well) were incubated with 0.03 to 10 nM $^{125}$I-L49 for 30 min. on ice, and then the cells were separated from unbound radioactivity by centrifugation through silicon oil. The tubes were frozen, the cell pellet was cut from the supernatant, and both fractions were counted in a gamma counter (Packard). Binding affinity and sites per cell were determined by Scatchard analysis (Trucco and dePetris, *Immunological Methods*, I. Lefkovits and B. Pernis, eds., Academic Press, New York, pp. 1–26 (1981)).

Soluble p97 (sp97). A secreted form of p97 (sp97) was made utilizing PCR based mutagenesis to introduce a stop codon at the cysteine residue three amino acids upstream of the glycophosphatidylinositol anchor domain (Alemany et al., *J. Cell Sci.*, 104:1155–1162 (1993); Food et al., *J. Biol. Chem.*, 269:3034–3040 (1994)). Briefly, the 3' oligonucleotide used in the PCR reaction contained the mutation changing the S710 codon to a stop codon. In all, the coding sequence for 29 amino acids was deleted from the carboxyl terminus of wild type p97. Cloning and expression of sp97 was accomplished using a glutamine synthetase gene as an amplifiable marker in CHO cells (Cockett et al., *Biotechnology*, 8:662–667 (1990)). The sp97 gene was cloned into pEE14 (Stephens and Cockett, *Nucl. Acids Res.*, 17:7110 (1989)) and transfected into CHO-K1 cells by calcium phosphate coprecipitation. Transformants were initially selected for resistance to 25 $\mu$M methionine sulfoximine, and sp97 secreting colonies were selected for amplification at drug concentrations of 100, 250, and 500 $\mu$M. The selection and amplification media used was Glasgow Minimum Essential Medium without L-glutamine, tryptose phosphate broth or sodium bicarbonate supplemented with 10% dialyzed fetal bovine serum. A cloned CHO cell line secreting sp97 was cultured in 10-shelf cell factories containing 1.5 liters of media.

Soluble p97 was isolated on a 96.5 immunoaffinity chromatography column as described for the purification of wild type p97 from melanoma cells (Baker et al., *FEBS Lett.*, 298:215–218 (1992)). Small amounts of residual contaminants were removed by gel filtration on a Sephacryl S300 HR column (Pharmacia LKB) using PBS as eluant. Solutions containing sp97 were concentrated by ultrafiltration to 1–5 mg/ml, sterilized by passage through a 0.1$\mu$ filter, and stored at 2-8° C. for up to 6 months without noticeable loss of biochemical or biological activity.

Cloning of L49 Variable Regions and sFv Construction. Construction of L49-sFv-bL by hybridization insertion was performed with materials and protocols from the BioRad M13 mutagenesis kit, except for isolation of single stranded phagemid template (Qiagen M13 kit, M13KO7 helper phage). The variable regions of the L49 antibody were cloned from the corresponding hybridoma mRNA by reverse transcription-PCR (Perkin Elmer GeneAmp reagents and Model 9600 thermal cycler), using random hexamer primed reverse transcription reactions and signal sequence and constant region PCR primers (Jones et al., *Biotechnology*, 9:88–92 (1991)). Construction of L49-sFv-bL began with a single-stranded template of the pET-26b phagemid containing the r2-1 mutant of the *Enterobacter cloacae* P99 bL gene (Siemers et al., *Biochemistry*, 35:2104–2111 (1996)) fused to the pelB leader sequence. Hybridization mutagenesis was used to insert the 218 linker sequence (Whitlow et al., *Protein Enq.*, 6:989–995 (1993)) (chemically synthesized oligonucleotide, 5'-TTCTGACACTGGCGTGCCCTTGGTAGAGCCTTC-GCCAGAGCCCGGTTTGCCAGAGCCGGACGTCGAG-CCGGCCATCGCCGGCTG-3'(SEQ ID. NO: 14)) and full $V_H$ and $V_L$ region sequences (oligonucleotides produced by asymmetric PCR, $V_H$ forward primer: 5'-CCAGCCGGC-GATGGCCGAGGTGCAGCTTCAGGAGT-3'(SEQ ID. NO: 15); $V_H$ reverse primer: 5'-AGAGCCGGACGTCG-AGCCTGAGGAGACGGTGACAGAGG-3'(SEQ ID. NO: 16); $V_L$ forward primer: 5'-AGGCTCTACCAAGGGCG-ATTTTGTGATGACCCAAAC-3' (SEQ ID. NO: 17); $V_L$ reverse primer: 5'-TTCTGACACTGGCGTCCGTTTGA-TTTCCAGCTTGG-3' (SEQ ID. NO: 18) in between the pelB leader sequence and bL in a 5'-pelB-$V_H$-218-$V_L$-bL-3' orientation. The nucleotide (SEQ ID NO: 19) and amino acid (SEQ ID NO: 20) sequences of L49-sFv-bL are provided in FIGS. 4A and 4B.

Expression, Purification and Characterization of L49-sFv-bL. L49-sFv-bL was expressed as a soluble protein in *E. coli* strain BL21 (λDE3) at 23° C. in 4L, baffled shake flasks. T-broth (1L) containing 30 μg/ml kanamycin was inoculated with several colonies of freshly transformed BL21 (λDE3) cells. The flasks were shaken (200 rpm) at 37° C. until the absorbance at 660 nm reached 0.8. The culture was cooled to 23° C. and IPTG (50 μM) was added. The culture was incubated with shaking for an additional 16 h at 23° C., at which time the absorbance at 660 nm was between 8–15. The cells were pelleted by centrifugation and resuspended in 30 mM Tris, 2 mM EDTA, 0.3% (v/v) Nonidet P-40, pH 8.5, 4° C. The mixture was stirred gently for 1 h, repelleted, and the supernatant was decanted and filtered (0.2 μm).

Purification of L49-sFv-bL was accomplished by a two-step affinity purification. The periplasmic fraction was first applied to a Sepharose column of immobilized sp97 antigen. The column was washed with PBS until the absorbance at 280 nm reached the baseline level, and bound protein was eluted with pH 11.2 buffer (50 mM sodium phosphate, 100 mM NaCl). Fractions containing the bound protein were neutralized with 1/10 v/v of 3M phosphate, pH 7.2. This material was then subjected to Sepharose 4B m-aminophenylboronic acid affinity chromatography (Cartwright et al., *Biochem. J.*, 221:505–512 (1984)) using washing and elution conditions described above. The resulting preparation was dialyzed against PBS, filtered (0.2 μm), and stored at 4° C. (0.1–1.1 mg/ml).

Competition binding experiments were performed as described by Svensson et al.(*Bioconjugate Chem.*, 3:176–181 (1992)). Immunoassays were performed by coating polystyrene 96 well plates with sp97 (0.1 mL, 2 μg/ml in PBS, overnight, 4° C.) After blocking with specimen diluent (Genetic Systems Corp.) for 1 h at 22° C., the blocking solution was replaced with fresh specimen diluent (0.1 ml) containing serial dilutions of the samples. After 1 h at 22° C. the plates were washed, followed by development with 0.1 mL of a nitrocefin (O'Callaghan et al., *Antimicrobial Agents and Chemotherapy*, 1:283–288 (1972)) solution (0.1 mM in PBS/1% dimethylformamide, 15 min, 22° C. Absorbance measurements were read in an plate reader using a 490 nm filter with 630 nm as the reference wavelength.

In Vitro Cytotoxicity. 3677 melanoma cells were plated into 96-well microliter plates ($10^4$ cells/well in 100 μL of Iscove's Modified Dulbecco's Medium (IMDM) with 10% fetal bovine serum, penicillin (60 μg/ml), and streptomycin (100 μg/ml) and allowed to adhere overnight. For blocking experiments, the cells were incubated with unconjugated L49 at 1 μM for 30 min. prior to treatment with the L49 conjugates. The cells were treated with L49-sFv-bL or L49 Fab'-bL at 10 nM. After 30 min. at 4° C., the plates were washed three times with antibiotic-free RPMI 1640 media (Gibco) with 10% fetal bovine serum, and then varying concentrations of CCM (FIG. 1) were added. CCM and PDM were also added to cells treated with media alone. After 1 h at 37° C., cells were washed three times with IMDM and incubated approximately 18 h at 37° C. The cells were then pulsed for 12 h with [$^3$H] thymidine (1 μCi/well) at 37° C., detached by freezing at −20° C. and thawing, and harvested onto glass fiber filter mats using a 96-well harvester (Wallac, Gaithersburg, Md.). Radioactivity was counted using a LKB Wallac β-plate counter.

In Vitro Cytotoxicity. 3677 melanoma cells were plated in 96-well microtiter plates ($10^4$ cells/well in 100 μL of IMDM with 10% fetal bovine serum, 60 μg/ml penicillin and 0.1 mg/ml streptomycin) and allowed to adhere overnight. For blocking experiments, the cells were incubated with unconjugated L49 at 1 μM for 30 min prior to treatment with the L49 conjugates. The cells were treated with L49-sFv-bL or L49 Fab'-bL at 10 nM. After 30 min at 4° C., the plates were washed three times with antibiotic-free RPMI 1640 media (Gibco) with 10% fetal bovine serum, and then varying concentrations of CCM were added. CCM and PDM were also added to cells treated with media alone. After 1 h at 37° C., cells were washed three times with IMDM and incubated approximately 18 h at 37° C. The cells were then pulsed for 12 h with [$^3$H] thymidine (1 μCi/well) at 37° C., detached by freezing at −20° C. and thawing, and harvested onto glass fiber filter mats using a 96-well harvester. Radioactivity was counted using a LKB Wallac β-plate counter.

Conjugate Localization. Subcutaneous 3677 melanoma tumors were established in female athymic nu/nu mice (8–12 weeks old, Harlan Sprague-Dawley, Indianapolis, Ind.) by transplanting tumors that had been previously passaged as previously described (Kerr et al., *Cancer Res.*, 55:3558–3563 (1995)). Tumor bearing mice were injected i.v. with L49-sFv-bL (1 or 4 mg mAb component/kg) or with L49-Fab'-bL (1.8 mg mAb component/kg). At various time intervals, the mice were anesthetized, bled through the orbital plexus, and sacrificed. Tissues were removed and homogenized in PBS containing 15 μg/ml aprotinin (2 mL/g tissue). To the homogenate was added 50 mM sodium phosphate containing 100 mM NaCl at pH 11.2 (10 ml/g tissue), and the suspension was mixed. After 20 min at room temperature, 3M sodium phosphate at pH 7.0 was added (2 ml/g tissue), and the mixture was mixed and centrifuged.

Quantification of conjugate concentrations was accomplished using a direct enzyme immunoassay. Polystyrene 96-well microtiter plates were coated with an affinity-purified rabbit polyclonal antisera to wild type *E. cloacae* bL (1 μg/ml), and were then blocked with specimen diluent (Genetic Systems Corp.). Serially diluted tissue extracts or purified samples (L49-sFv-bL as a standard for the fusion protein samples, L49-Fab'-bL as a standard for the L49-Fab'-bL samples) were added to the wells and allowed to bind for 3 h at room temperature. The plates were washed and developed by the addition of 0.1 ml of nitrocefin (O'Callaghan et al., *Antimicrobial Agents and Chemotherapy*, 1:283–288 (1972)) at 0.1 mM in PBS containing 1% dimethylformamide. Absorbance measurements were read in an ELISA plate reader using a 490 nm filter with 630 nm as the reference wavelength.

In Vivo Therapy Experiments. 3677 tumor-bearing mice (subcutaneous implants, six animals/group, average tumor volume 130 mm$^3$) were injected with L49-sFv-bL (i.v., 7–8 days post tumor implant), followed 12–48 h later by CCM using doses of fusion protein and prodrug as indicated in the Results section. Treatment with L49-sFv-bL+CCM was repeated 1 week later. Animals were monitored 1–2 times/week for body weight, general health, and tumor growth. Tumor volume was estimated using the formula: longest length×perpendicular dimension$^2$/2. Cures were defined as an established tumor that, after treatment, was not palpable for $\geq$10 tumor volume doubling delays ($\geq$40 days in the 3677 tumor model). Maximum tolerated doses led to less than 20% weight loss, no treatment-related deaths, and were within 50% of the dose where such events took place.

RESULTS

Figure 2:
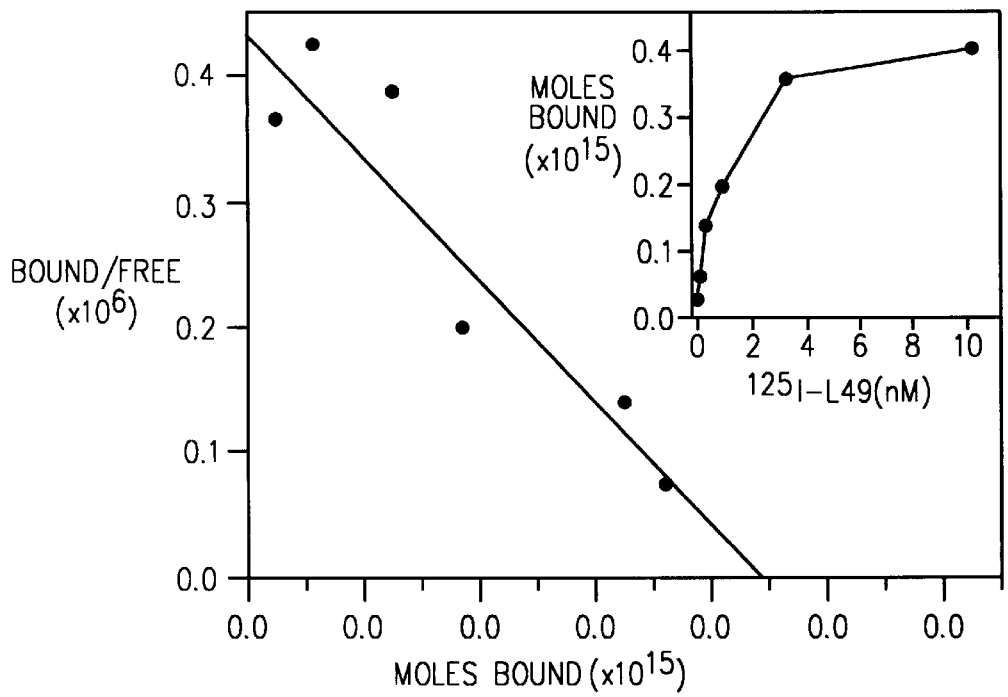
FIG. 2 depicts Scatchard binding analysis of L49 antibody binding to 3677 melanoma cells.

Characterization of the L49 Antibody. The L49 antibody (IgG1) binds to the p97 antigen, which has been shown to be present on most human melanomas and many carcinomas (Brown et al., *J. Immun.*, 127:539–545 (1981), Brown et al., *Proc. Natl. Acad. Sci.* (USA), 78:539–543 (1981); Woodbury et al., *Proc. Natl. Acad. Sci.* (USA), 77:2183–2187 (1980)). Scatchard analysis of the binding of radiolabeled L49 to the 3677 human melanoma cell line indicated that the mAb bound with a dissociation constant of 1.0 nM (FIG. 2). At saturation, there were approximately $2.1 \times 10^4$ molecules of L49 bound/cell. These values are very similar to those obtained for the 96.5 mAb (Kerr et al., *Cancer Res.* 55:3558–3563 (1995)), which also binds to p97, but to a different epitope than L49 (data not shown).

Cloning and Expression of L49-sFv-bL. The variable region genes for the L49 antibody heavy and light chains were cloned from the L49 hybridoma line by RT-PCR of hybridoma mRNA and amplification of the corresponding cDNA. A consensus sequence was determined by examining several clones from independent reverse transcription reactions to reduce the possibility of reverse transcription or PCR derived errors. The PCR primers used were complementary to the signal sequence and constant region of the mAb. Thus, the entire variable regions were obtained.

Figure 3:
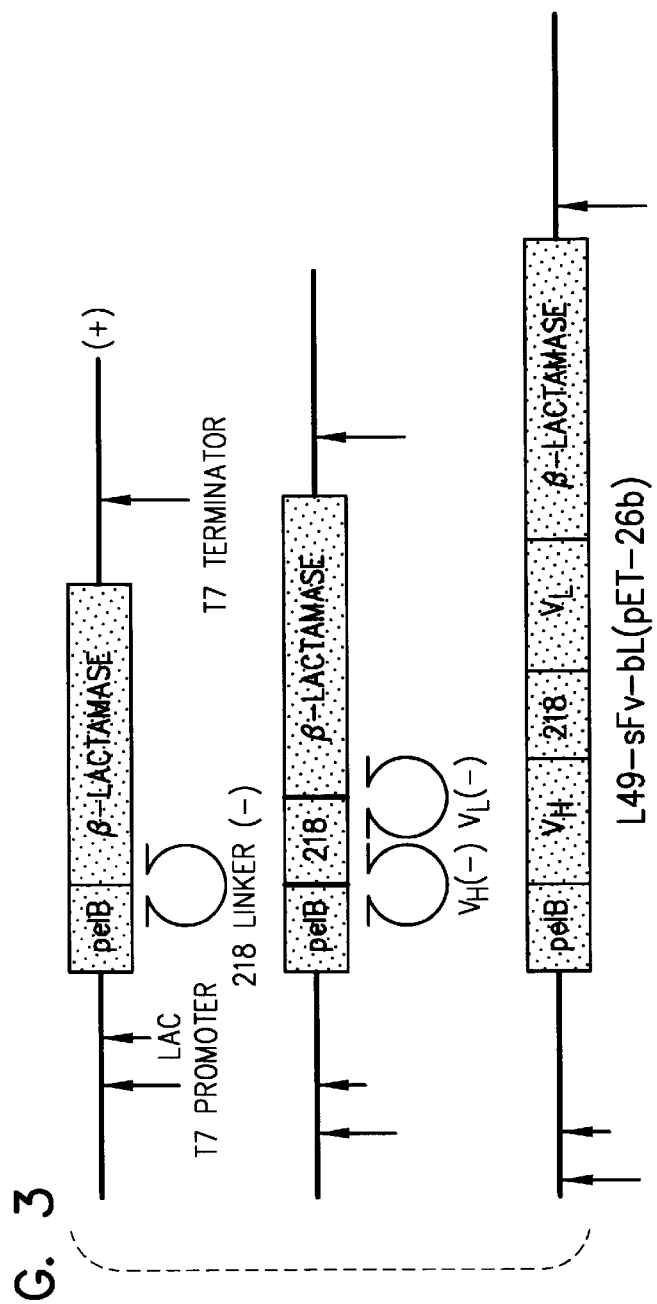
FIG. 3 depicts the construction of L49-sFv-bL. Three successive hybridization insertion reactions were used to install the 218 linker, variable heavy chain sequences, and variable light chain sequences into a pET phagemid containing the r2-1 mutant of the *E. cloacae* β-lactamase. Single stranded phagemid DNA was produced by infection of XL-I Blue carrying the pET phagemids with M13KO7 helper phage. An oligonucleotide coding for the 218 linker sequence (- strand), with complementary regions to the 3' end of the pelB sequence and the 3' end of the β-lactamase gene was prepared by chemical synthesis. Corresponding $V_H$ and $V_L$ sequences (- strand) were generated by asymmetric PCR.

L49-sFv-bL was constructed in a stepwise fashion by hybridization insertion of the sFv linker, $V_H$, and $V_L$ region sequences onto a single stranded pET phagemid template containing the pelB leader sequence and bL gene (FIG. 3). The particular bL gene used encoded a mutated form of bL (r2-1) that contained the sequence Thr Ser Phe Gly Asn (SEQ ID. NO: 2) at positions 286–290. This mutated bL has been shown to have slightly greater activity than the wild type enzyme (Siemers et al., *Biochemistry*, 35:2104–2111 (1996)). The 218 linker sequence corresponds to amino acids Gly Ser Thr Ser Gly Ser Gly Lys Pro Gly Ser Gly Glu Gly Ser Thr Lys Gly (SEQ ID. NO: 13), and was used as the sFv linker based on its ability to reduce sFv protein aggregation (Whitlow et al., *Protein Eng.*, 6:989–995 (1993)). An oligonucleotide coding for the 218 linker (- strand, produced by chemical synthesis) was first annealed to the phagemid template, resulting in a pelB-218-bL construct. $V_H$ and $V_L$ region segments (produced by asymmetric PCR) were then inserted into the intermediate construct to generate the final L49-sFv-bL gene in an pelB-$V_H$-218-$V_L$-bL orientation. The pelB leader sequence results in transport of the protein into the periplasmic space of *E. coli*. No additional linker was placed between $V_L$ and the bL enzyme. The nucleotide (SEQ ID NO: 19) and amino acid (SEQ ID NO: 20) sequences are provided in FIGS. 4A and 4B.

Figure 5A:
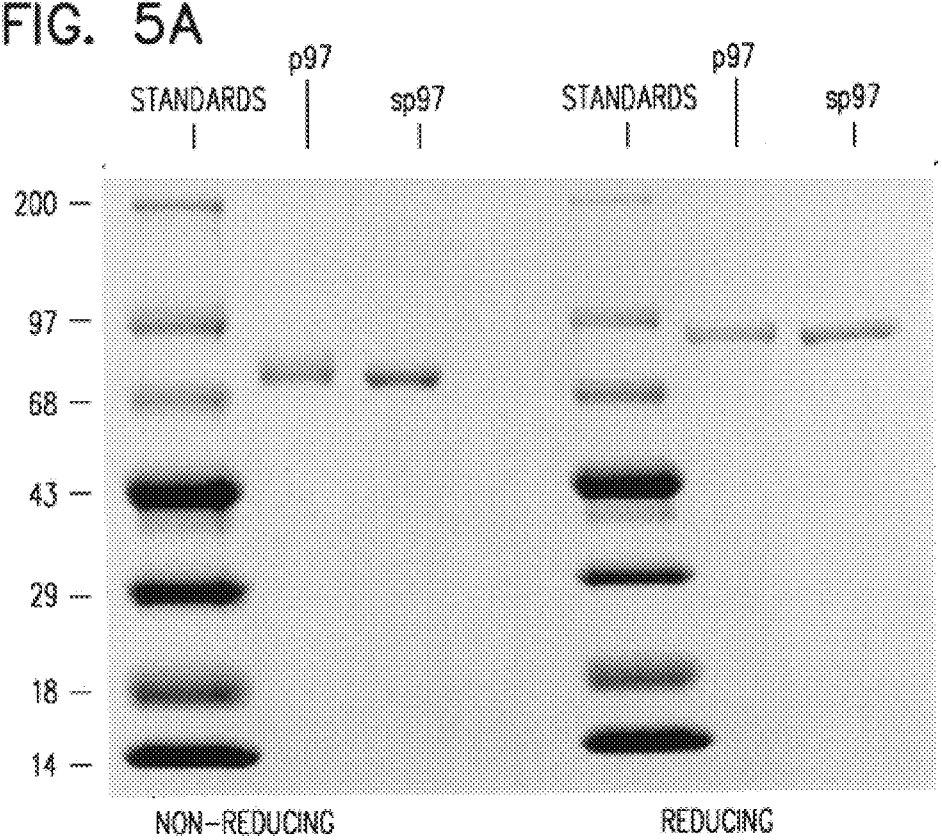
FIGS. 5A and 5B depict SDS-PAGE (4–20%) and isoelectric focusing analyses (pH 3–10) of recombinant sp97 and wild type p97 antigen.
Figure 5B:
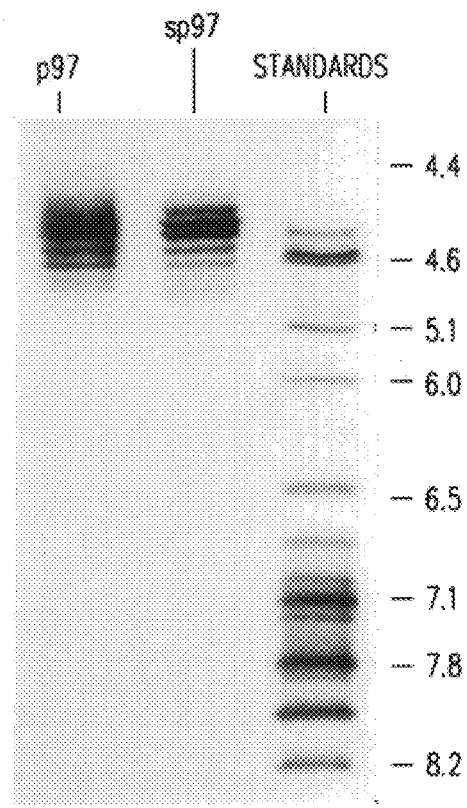

To facilitate the isolation and characterization of L49-containing fusion proteins, a soluble form of the p97 antigen was developed. This was made by truncating the p97 antigen at a site upstream to the membrane anchoring domain. The soluble antigen (sp97) was expressed in CHO-K1 cells and purified by affinity chromatography. SDS-PAGE analysis of recombinant sp97 indicated that it was slightly lower in molecular weight than p97 (FIG. 5A). Isoelectric focussing revealed little difference between p97 and sp97 (FIG. 5B), a result that was anticipated, since only a single charged residue is lost in the sp97 construct.

Figure 6A:
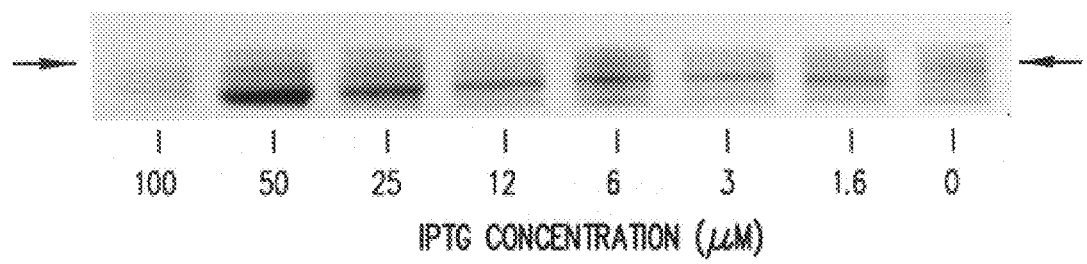
FIGS. 6A–6D depict SDS-PAGE analyses of L49-sFv-bL expression and purification.

L49-sFv-bL was expressed in soluble form in an *E. coli* strain that was transformed with the plasmid shown in FIG. 3. Quantitation of L49-sFv-bL containing samples was performed using an immunoassay in which the L49 portion was captured onto microtiter plates that were coated with sp97, and the bL enzyme activity was determined using nitrocefin as a calorimetric indicator for bL activity (O'Callaghan et al., *Antimicrobial Agents and Chemotherapy*, 1:283–288 (1972)). Thus, only bifunctional fusion protein was measured. Under the transcriptional control of the T7 promoter and lac operon, fusion protein expression could be detected by SDS-PAGE analyses of cell pellets when at IPTG concentrations as low as 1.6 $\mu$M (FIG. 6A). Significant levels of toxicity were observed when the IPTG concentration exceeded 90 $\mu$M, resulting in inhibition of cell growth and in the eventual outgrowth of cell populations that did not express fusion protein. Typically, 50 $\mu$M IPTG induction was used for large scale experiments, since this led to higher levels of fusion protein expression without significant levels of cytotoxicity. It was also found that expression of L49-sFv-bL was enhanced at lower temperatures, such that protein yields were higher at 23 or 30° C. compared to 37° C. Similar results have been noted for the expression of antibody fragments and other recombinant proteins in *E. coli* (Plückthun, *Immun. Rev.*, 130:151–188 (1992)).

Figure 6B:
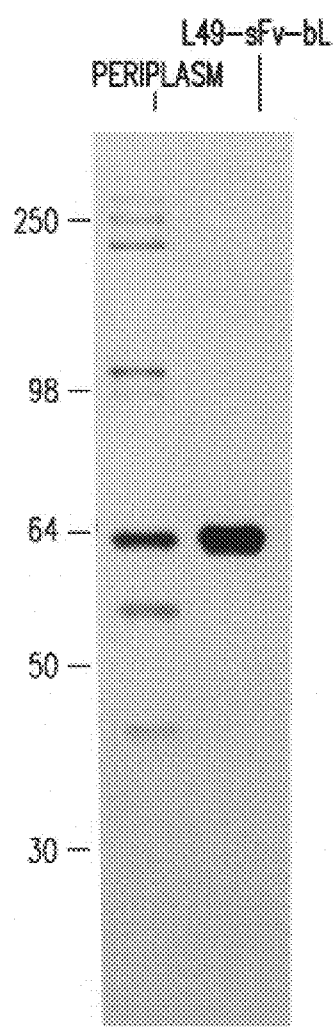

In shake flask cultures, 80% of active material was present in the periplasm of the bacterial cells, with the remainder present in the culture supernatant. Conventional techniques for releasing the periplasmic contents, such as sucrose/lysozyme spheroplasting or osmotic shock, resulted in only a limited release of the available protein. Similar results were also obtained using 20% alone. Freeze-thawing or sonication of cells to release total cytoplasmic material did not result in an increased yield of functional fusion protein. It was found that a high yield of fusion protein could be obtained by treating cell pellets with the detergent Nonidet-P-40. Expression levels of L49-sFv-bL using this detergent ranged from 2.5–8 mg/L culture. Western analysis (FIG. 6B) with a rabbit polyclonal antisera raised to bL showed that most of the bL containing protein in the preparation was approximately 63 kDa in molecular weight (theoretical molecular weight 66.5 kDa). Small amounts of truncated fragments and aggregated material were also detected.

Figure 6C:
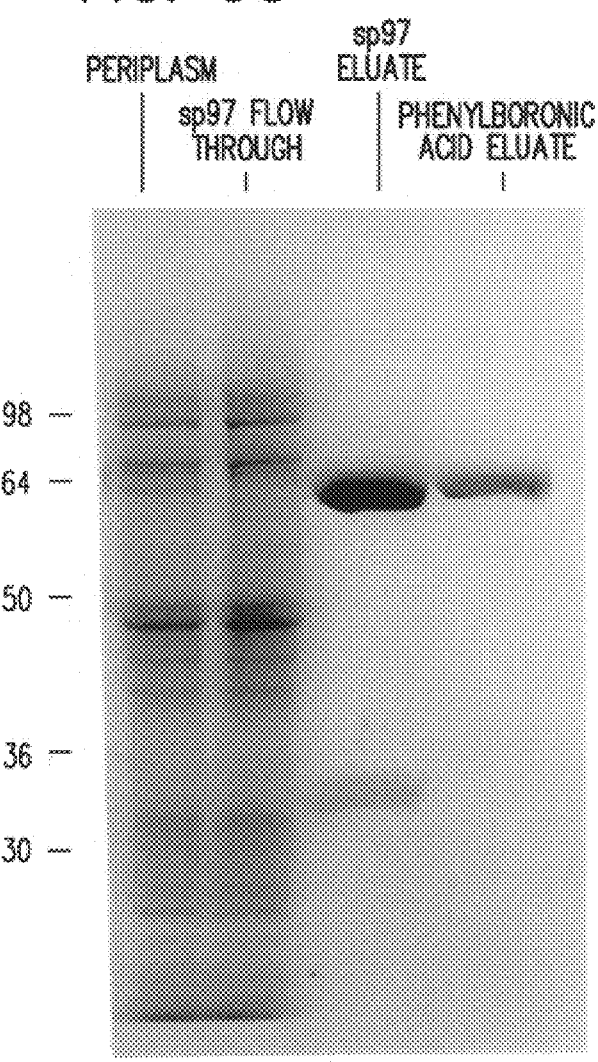
Figure 6D:
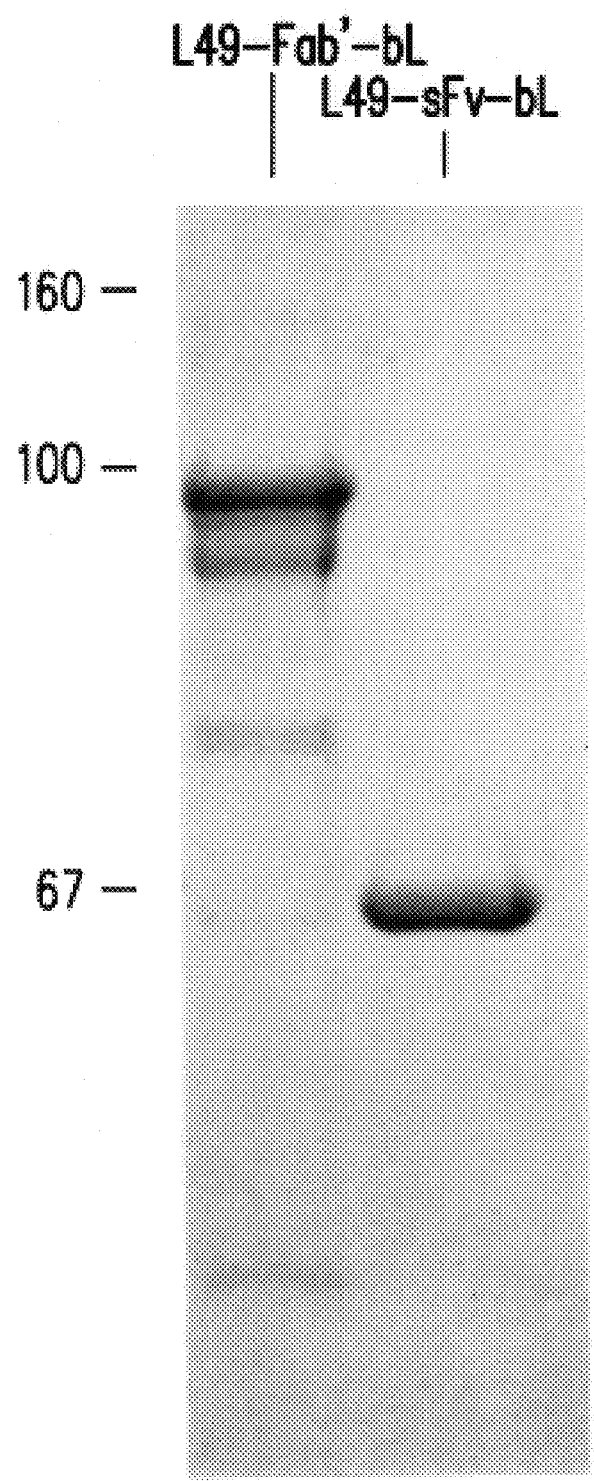

Purification of L49-sFv-bL. The purification of L49-sFv-bL to homogeneity was achieved by a two-step affinity chromatography procedure. Periplasmic preparations from shake flask cultures were first applied to an immobilized sp97 affinity column that was capable of binding to the L49 portion of the conjugate. After extensive washing, bound material was eluted at pH 11.2 (FIG. 6C). Acidic pH conditions (pH 2.2) successfully eluted the fusion protein but caused precipitation of material when working with multi-milligram quantities of fusion protein. The sp97 chromatography purified material was approximately 70% pure by size-exclusion HPLC and SDS-PAGE, with the contaminants consisting of two bands of approximately 33 kDa molecular weight. The second step of the purification involved binding the material to immobilized phenylboronic acid. This resin has previously been found to bind to β-lactamases, presumably to the active site of the enzymes (Cartwright and Waley, *Biochem. J.* 221;505–512 (1984)). This led to the recovery of protein that was pure by SDS-PAGE analysis (FIGS. 6C and 6D).

L49-sFv-bL Characterization and Activity. In view of the detergent based release of L49-sFv-bL from the bacteria, it was important to demonstrate that isolated fusion protein had been correctly processed and transported into the periplasm, such that the pelB leader sequence was cleaved from the amino terminus of the $V_H$ region. This was determined by subjecting the purified fusion protein to amino acid sequence analysis. The sequence obtained (Glu Val Leu Gln Leu Glu Ser (SEQ ID. NO: 21)) was identical to the expected $V_H$ amino terminal sequence, indicating that the leader sequence was proteolytically clipped, as designed.

Figure 7:
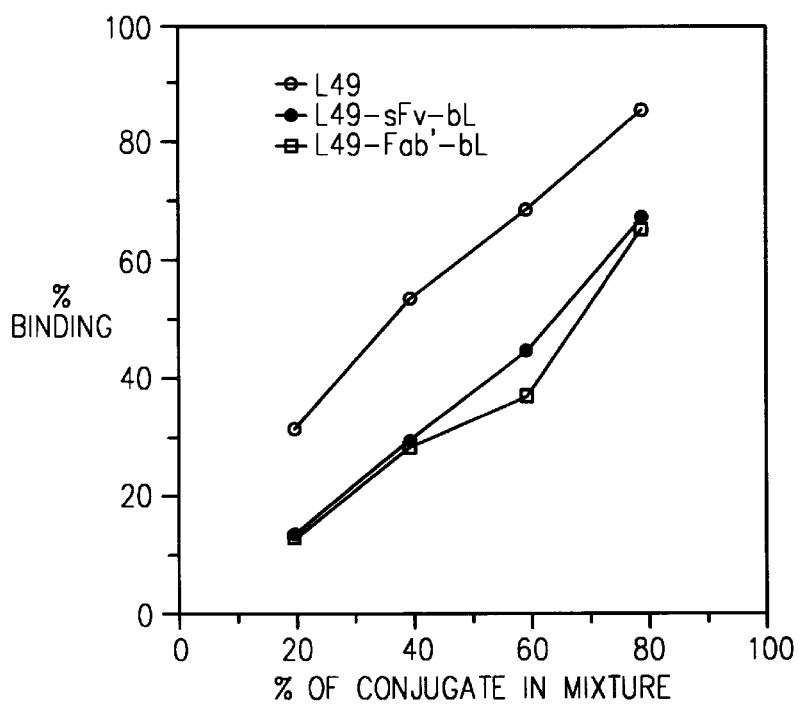
FIG. 7 depicts a competition binding assay. 3677 cells were incubated with various combinations of the test samples (L49, L49-sFv-bL, L49-Fab'-bL, and FITC-modified whole L49, keeping the total mAb concentration (test sample+L49-FITC) constant at 400 nM. Fluorescence intensity was determined by fluorescence activated cell sorter analysis.

The binding characteristics of the sFv portion of the fusion protein were determined using a fluorescent activated cell sorting competition assay in which fusion protein and FITC-modified whole L49 competed for binding to cell-surface antigens on SK-MEL 28 melanoma cells. L49-sFv-bL and the L49 Fab'-bL chemical conjugates bound equally well to the cell line, indicating that the binding activity of the antibody portion of the conjugate was preserved (FIG. 7). More detailed information about binding was obtained using surface plasmon resonance, which allowed the measurement of the on and off rates of L49-sFv-bL binding to the p97 antigen immobilized on a gold surface (Table 1). This assay established that the binding affinity of the fusion protein to the p97 antigen ($K_d$=1.0 nM) was comparable to L49 Fab' ($K_d$=0.73 nM), and chemically produced L49-Fab'-bL conjugate ($K_d$=1.3 nM).

TABLE 1

Binding and enzyme kinetic parameters of L49 and bL containing proteins

| Sample | $k_{on}$ ($M^{-1} \cdot s^{-1}$) | $k_{off}$ ($s^{-1}$) | $k_D$ (nM) | $k_{cat}$ ($s^{-1}$) | $k_m$ (μM) |
|---|---|---|---|---|---|
| L49 Fab' | $2.3 \times 10^5$ | $1.7 \times 10^{-4}$ | 0.73 | n.a.[b] | n.a. |
| r2-1 bL[c] | n.a. | n.a. | n.a. | 261 | 19 |
| L49-Fab'-bL[d] | $1.8 \times 10^5$ | $2.4 \times 10^{-4}$ | 1.3 | n.d.[e] | n.d. |
| L49-sFv'-bL[c] | $4.1 \times 10^5$ | $4.2 \times 10^{-4}$ | 1.0 | 232 | 19 |

[a]Values shown are the average of a minimum of two independent experiments, except for L49-Fab'-bL (binding experiment performed once). The range of values obtained in Michaelis-Menten kinetic analyses were within 5% of the means.
[b]Not Applicable.
[c]The r2-1 bL contains mutations at positions 286–290 compared to the wild type enzyme (Siemers et al., Biochemistry 35:2104–2111 (1996)).
[d]Chemically prepared conjugate containing the wild type enzyme.
[e]Not determined.

Enzymatic activity assays of the bL portion of L49-sFv-bL were undertaken using nitrocefin as the enzyme substrate (Table 1). Michaelis-Menten kinetic analyses confirmed that the fusion protein retained the full enzymatic activity of the mutant bL, enzyme from which it was derived (Siemers et al., *Biochemistry*, 35:2104–2111 (1996)). Thus, both the binding of the L49 antibody and enzymatic activity of the *E. cloacae* r2-1 bL were preserved in the fusion protein.

Figure 8:
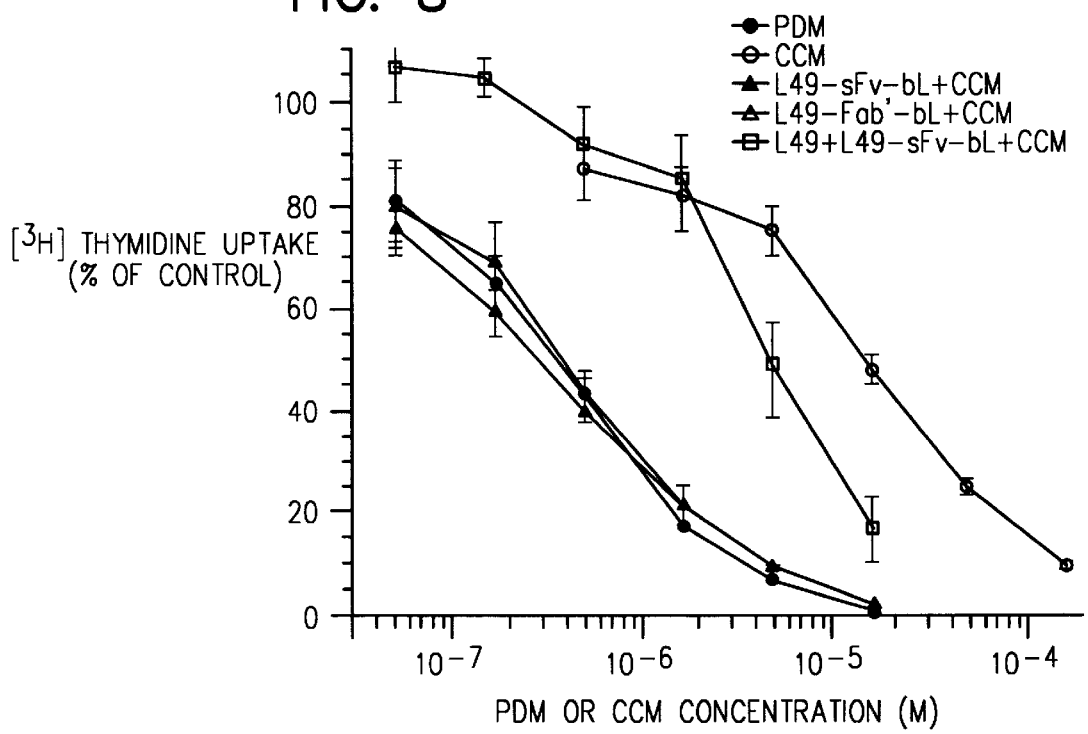
FIG. 8 depicts cytotoxic effects of mAb-bL+CCM combinations on 3677 melanoma cells as determined by the incorporation of [$^3$H]thymidine into DNA. 3677 cells were incubated with the mAb-bL conjugates, washed, and treated with CCM for 1 h. The effects were compared to cells treated with CCM or PDM for 1 h without prior conjugate exposure and to cells that were treated with saturating, amounts of unconjugated L49 prior to conjugate 1 treatment.

The cytotoxic effects of L49-sFv-bL in combination with CCM were determined on 3677 human melanoma cells, which express the p97 antigen. The experiments were performed by exposing the cells to the conjugates, and washing off unbound material before adding various concentrations of CCM. [$^3$H]-Thymidine incorporation was used to measure cytotoxic activity. The prodrug CCM ($IC_{50}$, 16 μM) was approximately 50-fold less toxic to 3677 cells than PDM ($IC_{50}$, 0.3 μM) As expected, L49-sFv-bL and L49-Fab'-bL were equally effective at prodrug activation, and the combinations were equivalent in activity to PDM (FIG. 8). This indicates that prodrug conversion was efficient under the conditions tested. In addition, it was found that activation was immunologically specific, since L49-sFv-bL did not activate CCM on cells that were previously saturated with L49 mAb before being exposed to the fusion protein.

In Vivo Localization. Biodistribution studies of L49-sFv-bL and L49-Fab'-bL were carried out in nude mice bearing subcutaneous (s.c.) 3677 melanoma tumor xenografts. The conjugates were injected i.v., and at various time points tissues were removed and extracted under alkaline conditions to disrupt antigen-antibody interactions. The samples were then trapped a polyclonal antiserum to bL, and bL activity was measured using nitrocefin as a colorimetric indicator (O'Callaghan et al, *Antimicrobial Agents and Chemotherapy*, 1:283–288 (1972)). Control experiments in which L49-sFv-bL was directly injected into excised tumors and tissues indicated that this extraction procedure recovered 90% of the injected bL activity.

Figure 9A:
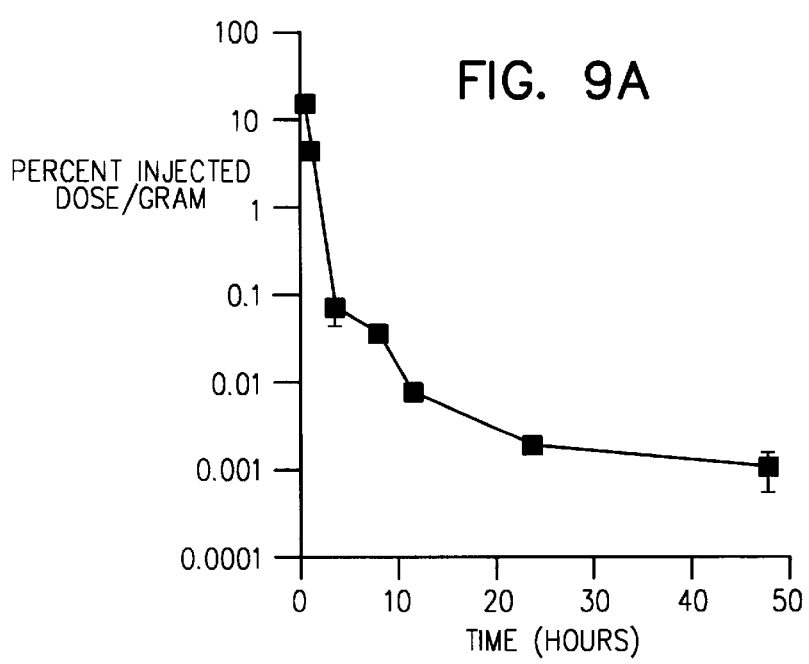

L49-sFv-bL cleared very rapidly from the blood (FIG. 9A). The initial and terminal clearance half lives ($t_{1/2}\alpha$ and $t_{1/2}\beta$) were 0.3 and 2.5 h, respectively, leading to a $10^4$ reduction of L49-sFv-bL blood levels within 24 h of conjugate administration. In spite of this rapid clearance, relatively high intratumoral levels of L49-sFv-bL were measured compared to normal tissues, and the ratio remained high for 24 h (FIG. 9B). At 4 h post L49-sFv-bL administration, the tumor to blood ratio was 13:1. The ratio increased substantially with time, and was 105:1 within 24 h of conjugate administration (Table 2).

TABLE 2

Tissue Distribution of Immunoconjugates

| | | % Injected dose/g (standard deviation) | | | | |
|---|---|---|---|---|---|---|
| Treatment[a] | Time | Tumor | Liver | Spleen | Kidney | Blood |
| L49-sFv-bL, 1 mg/kg | 4 hrs | 1.1 (0.2) | 0.021 (0.002) | 0.014 (0.008) | 0.027 (0.015) | 0.084 (0.04) |
| tumor/tissue ratios | | 1 | 52 | 79 | 41 | 13 |
| L49-sFv-bL, 1 mg/kg | 12 hrs | 0.53 (0.17) | <0.003 | <0.003 | <0.003 | 0.008 (0.001) |
| tumor/tissue ratios | | 1 | >177 | >177 | >177 | 66 |
| L49-sFv-bL, 1 mg/kg | 24 hrs | 0.21 (0.01) | <0.003 | <0.003 | <0.003 | 0.002 (0.001) |
| tumor/tissue ratios | | 1 | >70 | >70 | >70 | 105 |
| L49-sFv-bL, 4 mg/kg | 12 hrs | 0.73 (0.02) | <0.003 | <0.003 | <0.003 | 0.009 (0.001) |
| tumor/tissue ratios | | 1 | >240 | >240 | >240 | 81 |

TABLE 2-continued

Tissue Distribution of Immunoconjugates

| Treatment[a] | Time | Tumor | % Injected dose/g (standard deviation) | | | |
|---|---|---|---|---|---|---|
| | | | Liver | Spleen | Kidney | Blood |
| L49-sFv-bL, 4 mg/kg | 24 hrs | 0.29 (0.05) | <0.001 | <0.001 | <0.001 | 0.002 (0.0002) |
| tumor/tissue ratios | | 1 | >290 | >290 | >290 | 141 |
| L49-sFv-bL, 4 mg/kg | 48 hrs | 0.15 (0.07) | n.d.[b] | n.d. | n.d. | 0.001 (0.0002) |
| tumor/tissue ratios | | 1 | | | | 150 |
| L49-Fab'-bL, 1.8 mg/kg | 72 hrs | 0.28 (0.26) | 0.015 (0.003) | 0.010 (0.006) | 0.016 (0.005) | 0.05 (0.015) |
| tumor/tissue ratios | | 1 | 19 | 28 | 18 | 5.6 |

[a]Mice (3 animals/group) were injected with conjugates, and at the times indicated, tissues were excised and extracted to remove the conjugate. The percent injected dose was based on the measured bL activity compared to standard curves obtained from extracted tissues that were spiked with known amounts of L49-sFv-bL or L49-Fab'-bL.
[b]Not determined.

Similar results were obtained using L49-sFv-bL doses of 4 mg/kg. At this dose, very high tumor to blood ratios (141–151:1) were measured 24–48 h after the conjugate was administered. Interestingly, chemically produced L49-Fab'-bL cleared quite slowly from the blood and had only a 5.6:1 tumor to blood ratio 72 h after administration. Thus, L49-sFv-bL localizes in tumors, clears rapidly from the systemic circulation, and has significantly improved pharmacokinetic properties compared to the chemically produced L49-Fab'-bL conjugate.

Therapeutic Activity. In vivo therapy experiments were performed using the L49-sFv-bL/CCM combination in nude mice with established s.c. 3677 tumors. This particular tumor model has previously been shown to be resistant to treatment with doxorubicin, PDM, and CCM (Kerr et al., Cancer Res., 55:3558–3563 (1995)). In the experiments reported here, conjugate treatment was initiated 7–8 days after tumor implant, at which time the tumors were approximately 130 mm$^3$ in volume. CCM was then administered 12, 24, or 48 h later, and the treatment protocol was repeated after 1 week. Maximum tolerated doses are defined as those that led to less than 20% weight loss, no treatment-related deaths, and were within 50% of the dose where such events took place. A tumor was considered as having been cured once it was not palpable for at least 10 tumor volume doubling times, based on the tumor growth of untreated animals (tumor volume doubling time was 4 days). If an animal was removed from the experiment because of tumor growth, the data from the entire group was no longer plotted, but the remaining animals were followed for tumor size and general health.

Figure 10B:
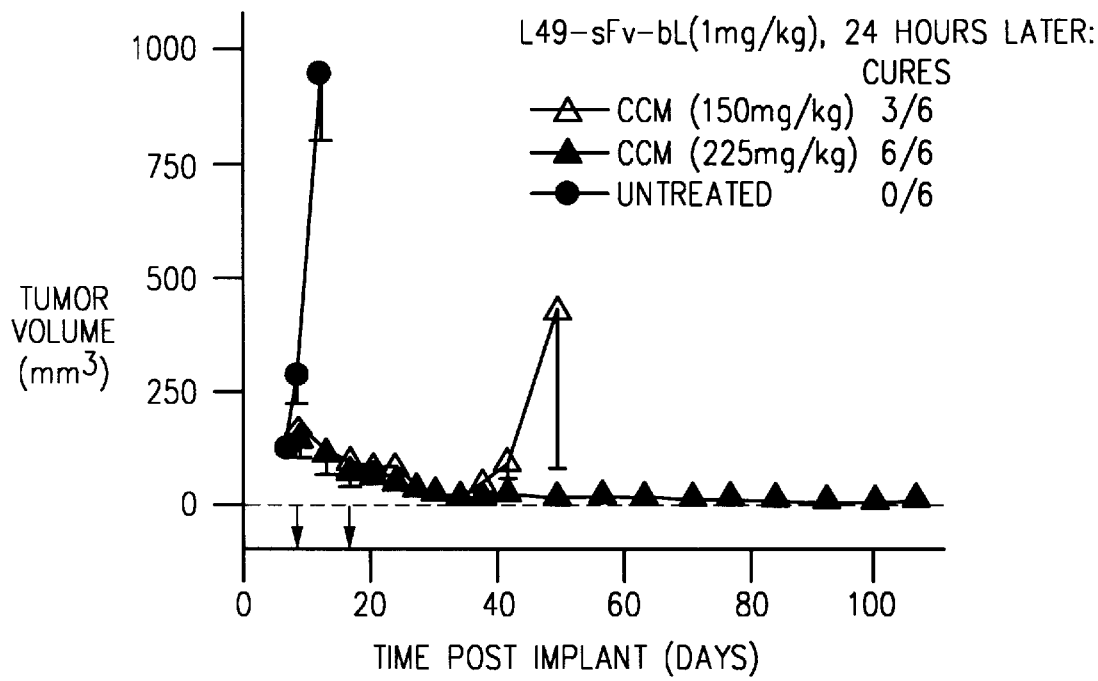

The maximum tolerated doses of CCM (300 mg/kg/injection) and PDM (3 mg/kg/injection) when administered weekly for three rounds induced 2 and 6 day delays in tumor outgrowth, respectively (data not shown). In contrast, pronounced antitumor activity was obtained in mice that received L49-sFv-bL prior to treatment with CCM (FIG. 10A). Therapeutic efficacy was schedule and dose dependent. Tumor cures were obtained in all of the animals that received CCM (125 and 175 mg/kg/injection ) 12 h after treatment with L49-sFv-bL (FIG. 10A). In this dosing schedule, significant antitumor activity including four cures in the group of six mice was obtained when the CCM dose was reduced to 75 mg/kg/injection. The remaining two animals in this group had tumors that underwent partial regressions, but eventually began to grow after the last prodrug treatment. There were no apparent toxicities in any of these treatment groups.

Figure 10C:
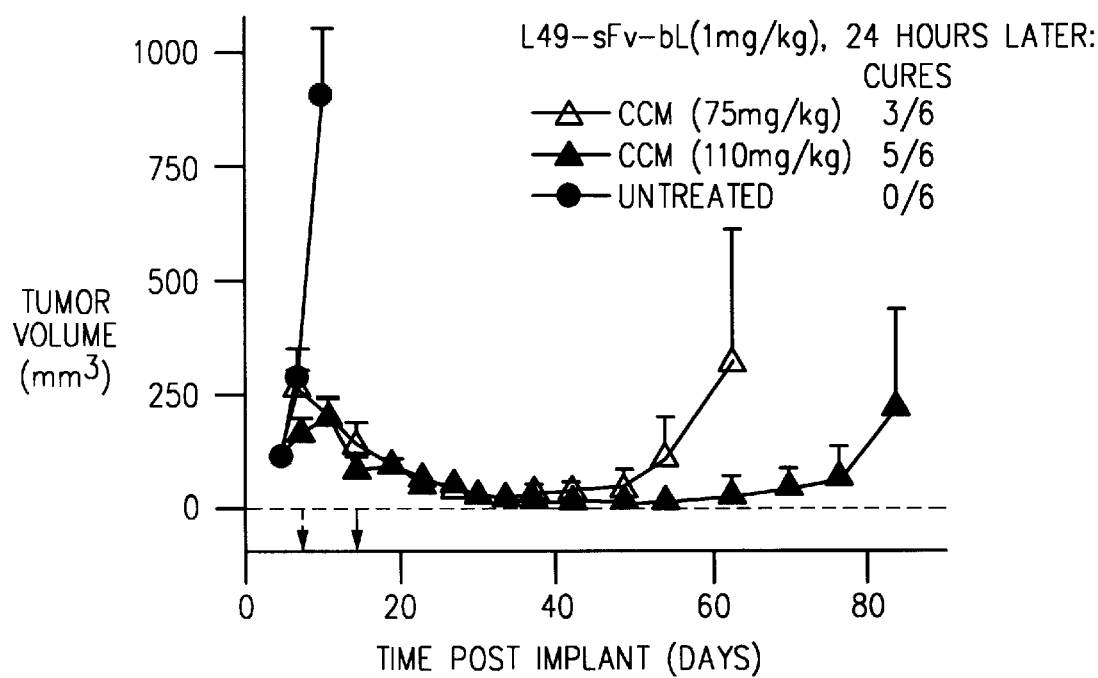
Figure 10D:
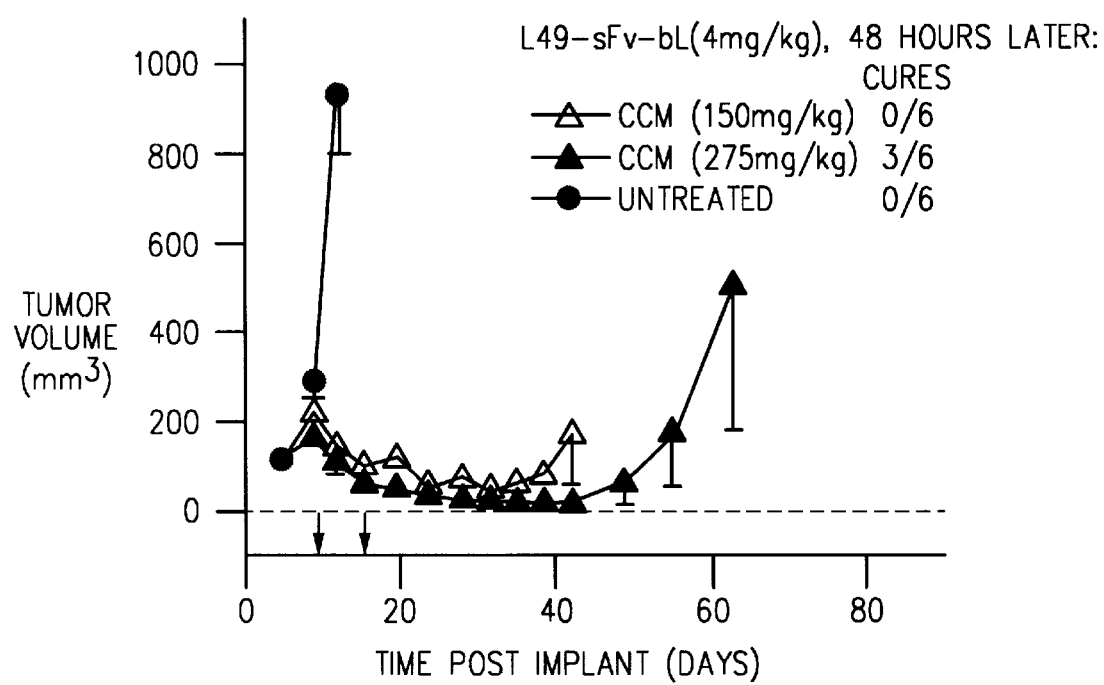

Significant antitumor activity could also be achieved when the prodrug was administered 24 h post conjugate administration, either by increasing the prodrug dose and keeping the conjugate dose constant at 1 mg/kg/injection (FIG. 10B), or by increasing the conjugate dose to 4 mg/kg/injection (FIG. 10C). In both cases, the majority of tumors were cured, again with no evidence of toxicity. Finally, therapeutic efficacy was also obtained with a 48 h interval between conjugate and prodrug administration (FIG. 10D). Tumor regressions were obtained in all of the mice in these groups, and three of six animals that received 275 mg/kg/injection CCM were cured. Thus, the antitumor activities of L49-sFv-bL in combination with CCM were pronounced, and therapeutic efficacy was achieved in a variety of dosing schedules.

In summary, the fusion protein L49-sFv-bL was constructed and expressed in E. coli as a soluble protein, and isolated from the periplasmic space using a two-stage affinity chromatography method. After purification, L49-sFv-bL was demonstrated to be homogeneous by SDS-PAGE, and was fully active with respect to both the L49 and bL components. As expected, the fusion protein was able to bind to melanoma cells that expressed the p97 antigen, and were able to activate a cephalosporin mustard in an immunologically specific manner.

To minimize systemic, non-targeted drug release in vivo, a high mAb-enzyme tumor to normal tissue ratio is needed before the anticancer prodrug is administered. To attain the required localization index in mice, the time between conjugate and prodrug administration has varied significantly from one conjugate to another. For example, the delay between conjugate and prodrug administration was 3 days for 96.5-Fab'-bL (molecular weight 92 kDa, Kerr et al., Cancer Res., 55:3558–3563 (1995)), 1 week for the anti CEA-Fab-β-glucuronidase fusion protein (molecular weight 250 kDa, Bosslet et al., Cancer Res., 54:2151–2159 (1994)), and 2 weeks for the ICR12-carboxypeptidase G2 conjugate (molecular weight range of 233–316 kDa, Eccles et al., Cancer Res., 54:5171–5177 (1994)). In some cases, it has even been necessary to accelerate systemic conjugate clearance in a separate step involving the formation of immune complexes before prodrug could be administered (Wallace et al., Cancer Res., 54:2719–2723 (1994); Kerr et al., Bioconjugate Chem., 4:353–357 (1993); Rogers et al., Br. J. Cancer, 72:1357–1363 (1995)). Here L49-sFv-bL not only clears very rapidly from the systemic circulation (FIG. 9A), but also preferentially localized into subcutaneous tumor xenografts (FIG. 9B, Table 2). The very high tumor to non-tumor fusion protein ratios obtained within 4–12 hours of conjugate treatment would lead to the prediction that, in contrast to other enzyme/prodrug systems (Bosslet et al., Cancer Res., 54:2151–2159 (1994); Eccles et al., Cancer Res., 54:5171–5177 (1994); Kerr et al., Cancer Res., 55:3558–3563 (1995)), therapeutic efficacy would not require protracted time intervals between conjugate and prodrug administration. This has now been experimentally confirmed, since cures of established tumors were obtained when CCM was administered 12 h following the conjugate (FIG. 10A).

It is noteworthy that a correlation can be made between the outcome in the therapy experiments (FIGS. 10A–D) and the pharmacokinetic data (FIGS. 9A and B and Table 2). At a given conjugate dose, the intratumoral concentration decreased with a half life of approximately 8 h (Table 2). This may be due to a variety of factors such as dissociation of the conjugate from the antigen, membrane recycling, enzyme metabolism, and rapid tumor growth. The net result is that longer time intervals between conjugate and prodrug administration require that either the amount of prodrug or conjugate be increased in order to maintain therapeutic efficacy (FIGS. 10A–D).

All references cited herein are specifically incorporated by reference in their entirety for all purposes.

Although the foregoing invention has been described in some detail by way of illustration and example for purposes of clarity of understanding, those with ordinary skill in the art will appreciate that other embodiments and variations of the invention are possible which employ the same inventive concepts described above. Therefore, the invention is not to be limited by the above disclosure, but is to be determined in scope by the claims which follow.

What is claimed is:

1. A fusion polypeptide comprising antibody variable light and heavy region amino acid sequences specific for a melanoma associated antigen operatively linked to a β-lactamase, wherein the fusion polypeptide comprises the amino acid sequence as shown in FIGS. 4A and 4B (SEQ ID. NO: 20).

2. The fusion polypeptide of claim 1, wherein the tumor cell antigen is p97.

3. A composition useful for treatment of melanoma which comprises a pharmaceutically effective amount of the fusion polypeptide of claim 1.

4. The composition of claim 3, further comprising a pharmaceutically acceptable carrier.

5. The composition of claim 3, further comprising a pharmaceutically acceptable adjuvant.

6. The composition of claim 3, wherein the composition is a liquid solution, a liquid suspension, a tablet, a pill, a powder, a suppository, a polymeric microcapsule, a microvessicle, a liposome, an injectable solution or an infusible solution.

7. The composition of claim 3, further comprising at least one prodrug which can be activated by the fusion polypeptide.

8. The composition of claim 7, wherein the prodrug is derived from a cephalosporin derivative of phenylenediamine mustard, doxorubicin, mitomycin C, paclitaxel, a vinca alkaloid or melphalan.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: Enterobacter cloacae

<400> SEQUENCE: 1

Gly Ser Asp Ser Lys
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 2

Thr Ser Phe Gly Asn
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 3

Ala Ser Ala Arg Arg
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 4

Asn Asn Ala Gly Tyr
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 5

Glu Val Glu Ile Lys
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 6

Leu Thr Ser Asn Arg
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 7

Gly Ser Lys Ser His
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 8

Val Thr Arg Asn Gln
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 9

Ile Val Asn Asn Lys
 1               5

<210> SEQ ID NO 10
<211> LENGTH: 5
<212> TYPE: PRT
<213> ORGANISM: Artificial Sequence
```

```
<220> FEATURE:
<223> OTHER INFORMATION: Description of Artificial Sequence:
      Substitutions for amino acid residues 537-541 of E. cloacae
      beta-lactamase.

<400> SEQUENCE: 10

Thr Ala Ile Pro Asp
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:
      Substitutions for amino acid residues 537-541 of E. cloacae
      beta-lactamase.

<400> SEQUENCE: 11

Ile Thr Lys Pro Asp
 1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence:
      Linker between VH and VL region sequences.

<400> SEQUENCE: 12

Gly Gly Gly Gly Ser Gly Gly Gly Ser Gly Gly Gly Gly Ser
 1               5                  10                  15

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence:
      Linker between VH and VL region sequences.

<400> SEQUENCE: 13

Gly Ser Thr Ser Gly Ser Gly Lys Pro Gly Ser Gly Glu Gly Ser Thr
 1               5                  10                  15

Lys Gly

<210> SEQ ID NO 14
<211> LENGTH: 84
<212> TYPE: DNA
<213> ORGANISM: Artificial Sequence
<220> FEATURE:
<223> OTHER INFORMATION: Description of Artificial Sequence:
      Hybridization mutagenesis sequence to insert the 218 linker
      sequence.

<400> SEQUENCE: 14
ttctgacact ggcgtgccct tggtagagcc ttcgccagag cccggtttgc cagagccgga      60
cgtcgagccg gccatcgccg gctg                                             84

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:
      VH forward PCR primer.
```

<400> SEQUENCE: 15
ccagccggcg atggccgagg tgcagcttca ggagt                35

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:
      VH reverse PCR primer.

<400> SEQUENCE: 16
agagccggac gtcgagcctg aggagacggt gacagagg            38

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      VL forward PCR primer.

<400> SEQUENCE: 17
aggctctacc aagggcgatt ttgtgatgac ccaaac              36

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence:
      VL reverse PCR primer.

<400> SEQUENCE: 18
ttctgacact ggcgtccgtt tgatttccag cttgg               35

<210> SEQ ID NO 19
<211> LENGTH: 2010
<212> TYPE: DNA
<213> ORGANISM: Artificial Sequence
<220> FEATURE:
<223> OTHER INFORMATION: Description of Artificial Sequence:
      Nucleotide sequence for L49-sFv-bL including PelB leader.

<400> SEQUENCE: 19
aattaatacg actcactata ggggaattgt gagcggataa caattcccct ctagaaataa    60
ttttgtttaa ctttaagaag gagatataca tatgaaatac ctgctgccga ccgctgctgc   120
tggtctgctg ctcctcgctg cccagccggc gatggccgag gtgcagcttc aggagtcagg   180
acctagcctc gtgaaacctt ctcagactct gtccctcacc tgttctgtca ctggcgactc   240
catcaccagt ggttactgga actggatccg gaagttccca gggaataaac ttgaatatat   300
gggttacata agcgacagtg gtatcactta ctacaatcca tctctcaaaa gtcgcatttc   360
catcactcga gacacatcca agaaccaata ctacctccag ttgaattttg tgactgctga   420
ggacacagcc acatataact gtgcaagaag gactctggct acttactatg ctatggacta   480
ctggggtcaa ggaacctctg tcaccgtctc ctcaggctcg acgtccggct ctggcaaacc   540
gggctctggc gaaggctcta ccaagggcga ttttgtgatg acccaaactc cactctccct   600
gcctgtcagt cttggagatc aagcctccat ctcttgcagg ctagtcaga gccttgtaca   660 cagtaatgga aacacctatt tacattggta cctgcagaag ccaggccagt ctccaaagct   720
cctgatctac agagtttcca accgattttc tggggtccca gacaggttca gtggcagtgg   780

```
atcagggaca gatttcacac tcaagatcag cagagtggag gctgaggatc tgggagttta      840
tttctgctct caaagtacac atgttcctcc gacgttcggt ggaggcacca agctggaaat      900
caaacggacg ccagtgtcag aaaaacagct ggcggaggtg gtcgcgaata cgattacccc      960
gctgatgaaa gcccagtctg ttccaggcat ggcggtggcc gttatttatc agggaaaacc     1020
gcactattac acatttggca aggccgatat cgcggcgaat aaacccgtta cgcctcagac     1080
cctgttcgag ctgggttcta taagtaaaac cttcaccggc gttttaggtg gggatgccat     1140
tgctcgcggt gaaatttcgc tggacgatgc ggtgaccaga tactggccac agctgacggg     1200
caagcagtgg cagggtattc gtatgctgga tctcgccacc tacaccgctg gcggcctgcc     1260
gctacaggta ccggatgagg tcacggataa cgcctccctg ctgcgctttt atcaaaactg     1320
gcagccgcag tggaagcctg gcacaacgcg tctttacgcc aacgccagca tcggtctttt     1380
tggtgcgctg gcggtcaaac cttctggcat gccctatgag caggccatga cgacgcgggt     1440
ccttaagccg ctcaagctgg accatacctg gattaacgtg ccgaaagcgg aagaggcgca     1500
ttacgcctgg ggctatcgtg acggtaaagc ggtgcgcgtt tcgccgggta tgctggatgc     1560
acaagcctat ggcgtgaaaa ccaacgtgca ggatatggcg aactgggtca tggcaaacat     1620
ggcgccggag aacgttgctg atgcctcact taagcagggc atcgcgctgg cgcagtcgcg     1680
ctactggcgt atcgggtcaa tgtatcaggg tctgggctgg gagatgctca actggcccgt     1740
ggaggccaac acggtggtcg agacgagttt tggtaatgta gcactggcgc cgttgcccgt     1800
ggcagaagtg aatccaccgg ctcccccggt caaagcgtcc tgggtccata aaacgggctc     1860
tactggcggg tttggcagct acgtggcctt tattcctgaa aagcagatcg gtattgtgat     1920
gctcgcgaat acaagctatc cgaacccggc acgcgttgag gcggcatacc atatcctcga     1980
ggcgctacag tagactagtg aattcgagct                                      2010
```

<210> SEQ ID NO 20
<211> LENGTH: 638
<212> TYPE: PRT
<213> ORGANISM: Artificial Sequence
<220> FEATURE:
<223> OTHER INFORMATION: Description of Artificial Sequence:
      Amino acid sequence for L49-sFv-bL including PelB leader

<400> SEQUENCE: 20

```
Met Lys Tyr Leu Leu Pro Thr Ala Ala Ala Gly Leu Leu Leu Leu Ala
 1               5                  10                  15

Ala Gln Pro Ala Met Ala Glu Val Gln Leu Gln Glu Ser Gly Pro Ser
                20                  25                  30

Leu Val Lys Pro Ser Gln Thr Leu Ser Leu Thr Cys Ser Val Thr Gly
            35                  40                  45

Asp Ser Ile Thr Ser Gly Tyr Trp Asn Trp Ile Arg Lys Phe Pro Gly
        50                  55                  60

Asn Lys Leu Glu Tyr Met Gly Tyr Ile Ser Asp Ser Gly Ile Thr Tyr
 65                  70                  75                  80

Tyr Asn Pro Ser Leu Lys Ser Arg Ile Ser Ile Thr Arg Asp Thr Ser
                85                  90                  95

Lys Asn Gln Tyr Tyr Leu Gln Leu Asn Phe Val Thr Ala Glu Asp Thr
            100                 105                 110

Ala Thr Tyr Asn Cys Ala Arg Arg Thr Leu Ala Thr Tyr Tyr Ala Met
        115                 120                 125

Asp Tyr Trp Gly Gln Gly Thr Ser Val Thr Val Ser Ser Gly Ser Thr
    130                 135                 140
```

-continued

Ser Gly Ser Gly Lys Pro Gly Ser Gly Glu Ser Thr Lys Gly Asp
145                 150                 155                 160

Phe Val Met Thr Gln Thr Pro Leu Ser Leu Pro Val Ser Leu Gly Asp
            165                 170                 175

Gln Ala Ser Ile Ser Cys Arg Ala Ser Gln Ser Leu Val His Ser Asn
            180                 185                 190

Gly Asn Thr Tyr Leu His Trp Tyr Leu Gln Lys Pro Gly Gln Ser Pro
            195                 200                 205

Lys Leu Leu Ile Tyr Arg Val Ser Asn Arg Phe Ser Gly Val Pro Asp
210                 215                 220

Arg Phe Ser Gly Ser Gly Ser Gly Thr Asp Phe Thr Leu Lys Ile Ser
225                 230                 235                 240

Arg Val Glu Ala Glu Asp Leu Gly Val Tyr Phe Cys Ser Gln Ser Thr
            245                 250                 255

His Val Pro Pro Thr Phe Gly Gly Gly Thr Lys Leu Glu Ile Lys Arg
            260                 265                 270

Thr Pro Val Ser Glu Lys Gln Leu Ala Glu Val Val Ala Asn Thr Ile
            275                 280                 285

Thr Pro Leu Met Lys Ala Gln Ser Val Pro Gly Met Ala Val Ala Val
            290                 295                 300

Ile Tyr Gln Gly Lys Pro His Tyr Tyr Thr Phe Gly Lys Ala Asp Ile
305                 310                 315                 320

Ala Ala Asn Lys Pro Val Thr Pro Gln Thr Leu Phe Glu Leu Gly Ser
            325                 330                 335

Ile Ser Lys Thr Phe Thr Gly Val Leu Gly Gly Asp Ala Ile Ala Arg
            340                 345                 350

Gly Glu Ile Ser Leu Asp Asp Ala Val Thr Arg Tyr Trp Pro Gln Leu
            355                 360                 365

Thr Gly Lys Gln Trp Gln Gly Ile Arg Met Leu Asp Leu Ala Thr Tyr
            370                 375                 380

Thr Ala Gly Gly Leu Pro Leu Gln Val Pro Asp Glu Val Thr Asp Asn
385                 390                 395                 400

Ala Ser Leu Leu Arg Phe Tyr Gln Asn Trp Gln Pro Gln Trp Lys Pro
            405                 410                 415

Gly Thr Thr Arg Leu Tyr Ala Asn Ala Ser Ile Gly Leu Phe Gly Ala
            420                 425                 430

Leu Ala Val Lys Pro Ser Gly Met Pro Tyr Glu Gln Ala Met Thr Thr
            435                 440                 445

Arg Val Leu Lys Pro Leu Lys Leu Asp His Thr Trp Ile Asn Val Pro
450                 455                 460

Lys Ala Glu Glu Ala His Tyr Ala Trp Gly Tyr Arg Asp Gly Lys Ala
465                 470                 475                 480

Val Arg Val Ser Pro Gly Met Leu Asp Ala Gln Ala Tyr Gly Val Lys
            485                 490                 495

Thr Asn Val Gln Asp Met Ala Asn Trp Val Met Ala Asn Met Ala Pro
            500                 505                 510

Glu Asn Val Ala Asp Ala Ser Leu Lys Gln Gly Ile Ala Leu Ala Gln
            515                 520                 525

Ser Arg Tyr Trp Arg Ile Gly Ser Met Tyr Gln Gly Leu Gly Trp Glu
            530                 535                 540

Met Leu Asn Trp Pro Val Glu Ala Asn Thr Val Val Glu Thr Ser Phe
545                 550                 555                 560

-continued

```
Gly Asn Val Ala Leu Ala Pro Leu Pro Val Ala Glu Val Asn Pro Pro
                565                 570                 575

Ala Pro Pro Val Lys Ala Ser Trp Val His Lys Thr Gly Ser Thr Gly
            580                 585                 590

Gly Phe Gly Ser Tyr Val Ala Phe Ile Pro Glu Lys Gln Ile Gly Ile
        595                 600                 605

Val Met Leu Ala Asn Thr Ser Tyr Pro Asn Pro Ala Arg Val Glu Ala
    610                 615                 620

Ala Tyr His Ile Leu Glu Ala Leu Gln Thr Ser Glu Phe Glu
625                 630                 635

<210> SEQ ID NO 21
<211> LENGTH: 7
<212> TYPE: PRT
<213> ORGANISM: Murine

<400> SEQUENCE: 21

Phe Val Leu Gln Leu Phe Ser
  1               5
```